US006130079A

United States Patent [19]
Ni et al.

[11] Patent Number: 6,130,079
[45] Date of Patent: Oct. 10, 2000

[54] RAIDD, A NOVEL DEATH ADAPTOR MOLECULE

[75] Inventors: Jian Ni, Rockville, Md.; Vishva M. Dixit, Los Altos Hills, Calif.

[73] Assignee: Human Genome Sciences, Inc., Rockville, Md.

[21] Appl. No.: 08/995,159

[22] Filed: Dec. 19, 1997

Related U.S. Application Data

[60] Provisional application No. 60/033,868, Dec. 20, 1996.

[51] Int. Cl.[7] .............................. C12N 9/50; C12N 15/00; C12N 1/20; C07H 21/04
[52] U.S. Cl. ................... 435/219; 435/320.1; 435/252.3; 536/23.2
[58] Field of Search .................................... 435/69.1, 219, 435/320.1, 252.3; 536/23.2, 23.1, 23.5

[56] References Cited

FOREIGN PATENT DOCUMENTS

WO 95/00160  1/1995  WIPO.
WO 96/26280  8/1996  WIPO.

OTHER PUBLICATIONS

BESTFIT program description, taken from Program Manual, Sequence Analysis Software Package, 1991.
Baglioni, C., "Mechanisms of Cytotoxicity, Cytolysis, and Growth Stimulation by TNF," In: *Tumor Necrosis Factors: The Molecules and Their Emerging Role in Medicine.* Beutler, B., ed., Raven Press, New York, NY, pp. 425–438 (1992).
Boldin, M.P. et al., "A Novel Protein That Interacts with the Death Domain of Fas/APO1 Contains a Sequence Motif Related to the Death Domain," *J. Biol. Chem.* 270(14):7795–7798 (Apr. 1995).
Boldin, M.P. et al., "Involvement of MACH, a Novel MORT1/FADD–Interacting Protease, in Fas/APO–1–and TNF Receptor–Induced Cell Death," *Cell* 85:803–815 (Jun. 1996).

Chinnaiyan, A.M. et al., "FADD, a Novel Death Domain–Containing Protein, Interacts with the Death Domain of Fas and Initiates Apoptosis," *Cell* 81:505–512 (May 1995).
Chinnaiyan, A.M. et al., "Molecular Ordering of the Cell Death Pathway," *J. Biol. Chem.* 271(9):4573–4576 (Mar. 1996).
Chinnaiyan, A.M. et al., "FADD:MORT1 Is a Common Mediator of CD95 (Fas/APO–1) and Tumor Necrosis Factor Receptor–induced Apoptosis," *J. Biol. Chem.* 271(9):4961–4965 (Mar. 1996).
Chinnaiyan, A.M. and V.M. Dixit, "The cell–death machine," *Curr. Biol.* 6(5):555–562 (May 1996).
Cleveland, J.L. and J.N. Ihle, "Contenders in FasL/TNF Death Signaling," *Cell* 81:479–482 (May 1995).
Duan, H. et al., "ICE–LAP3, a Novel Mammalian Homologue of the *Caenorhabditis elegans* Cell Death Protein Ced–3 Is Activated during Fas– and Tumor Necrosis Factor–induced Apoptosis," *J. Biol. Chem.* 271(3):1621–1625 (Jan. 1996).
Duan, H. et al., "ICE–LAP6, a Novel Member of the ICE/Ced–3 Gene Family, Is Activated by the Cytotoxic T Cell Protease Granzyme B," *J. Biol. Chem.* 271(28):16720–16724 (Jul. 1996).

(List continued on next page.)

*Primary Examiner*—Karen Cochrane Carlson
*Assistant Examiner*—Devesh Srivastava
*Attorney, Agent, or Firm*—Sterne, Kessler, Goldstein & Fox P.L.L.C.

[57] ABSTRACT

The present invention relates to a novel molecule involved in the process of apoptosis. In particular, isolated nucleic acid molecules are provided encoding the human RAIDD protein and splice variants thereof—referred to as RAIDD-SV1 and RAIDD-SV2. RAIDD polypeptides are also provided as are vectors, host cells and recombinant methods for producing the same. The invention further relates to screening methods for identifying agonists and antagonists of RAIDD activity.

92 Claims, 6 Drawing Sheets

OTHER PUBLICATIONS

Duan, H. and V.M. Dixit, "RAIDD is a new 'death' adaptor molecule," *Nature* 385:86–89 (Jan. 1997).

Ellis, H.M. and H.R. Horvitz, "Genetic Control of Programmed Cell Death in the Nematode *C. elegans*," *Cell* 44:817–829 (1986).

Enari, M. et al., "Involvement of an ICE–like protease in Fas–mediated apoptosis," *Nature* 375:78–81 (May 1995).

Higuchi, R. "A general method of in vitro preparation and specific mutagenesis of DNA fragments: study of protein and DNA interactions," *Nucl. Acids. Res.* 16(15):7351–7367 (1988).

Hsu, H. et al., "The TNF Receptor 1–Associated Protein TRADD Signals Cell Death and NF–kB Activation," *Cell* 81:495–504 (May 1995).

Hsu, H. et al., "TRADD–TRAF2 and TRADD–FADD Interactions Define Two Distinct TNF Receptor 1 Signal Transduction Pathways," *Cell* 84:299–308 (Jan. 1996).

Hsu, H. et al., "TNF–Dependent Recruitment of the Protein Kinase RIP to the TNF Receptor–1 Signaling Complex," *Immunity* 4:387–396 (Apr. 1996).

Itoh, N. et al., "The Polypeptide Encoded by the cDNA for Human Cell Surface Antigen Fas Can Mediate Apoptosis," *Cell* 66:233–243 (1991).

Itoh, N. and S. Nagata, "A Novel Protein Domain Required for Apoptosis," *J. Biol. Chem.* 268(15):10932–10937 (1993).

Kischkel, F.C. et al., "Cytotoxicity–dependent APO–1 (Fas/CD95)–associated proteins form a death–inducing signaling complex (DISC) with the receptor," *EMBO J.* 14(22):5579–5588 (Nov. 1995).

Lennon, G. et al., "The I.M.A.G.E. Consortium: An Integrated Molecular Analysis of Genomes and Their Expression," *Genomics* 33:151–152 (Apr. 1996).

Los, M. et al., "Requirement of an ICE/CED–3 protease for Fas/APO–1–mediated apoptosis," *Nature* 375:81–83 (May 1995).

Muzio, M. et al., "FLICE Induced Apoptosis in a Cell–free System," *J. Biol. Chem.* 272(5):2952–2956 (Jan. 1997).

O'Rourke, K.M. et al., "Thrombospondin 1 and Thrombospondin 2 Are Expressed as Both Homo– and Heterotrimers," *J. Biol. Chem.* 267(35):24921–24924 (1992).

Peter, M.E., et al., "CD95 (APO–1/Fas)–associated signalling proteins," *Cell Death & Differentiation* 3:161–170 (Apr. 1996).

Ray, C.A. et al., "Viral Inhibition of Inflammation: Cowpox Virus Encodes an Inhibitor of the Interleukin–1β Converting Enzyme," *Cell* 69:597–604 (1992).

Rothe, M. et al., "A Novel Family of Putative Signal Transducers Associated with the Cytoplasmic Domain of the 75 kDa Tumor Necrosis Factor Receptor," *Cell* 78:681–692 (1994).

Rothe, M. et al., "TRAF2–Mediated Activation of NF–kB by TNF Receptor 2 and CD40," *Science* 269:1424–1427 (Sep. 1995).

Shaham, S. and H.R. Horvitz, "Developing *Caenorhabditis elegans* neurons may contain both cell–death protective and killer activities," *Genes & Develop.* 10:578–591 (Mar. 1996).

Smith, C.A. et al., "A Receptor for Tumor Necrosis Factor Defines an Unusual Family of Cellular and Viral Proteins," *Science* 248:1019–1023 (1990).

Stanger, B.Z. et al., "RIP: A Novel Protein Containing a Death Domain That Interacts with Fas/APO–1 (CD95) in Yeast and Causes Cell Death," *Cell* 81:513–523 (May 1995).

Steller, H., "Mechanisms and Genes of Cellular Suicide," *Science* 267:1445–1449 (Mar. 1995).

Takahashi, A. and W.C. Earnshaw, "ICE–related proteases in apoptosis," *Curr. Opin. Genetics & Development* 6(1):50–55 (Feb. 1996).

Tartaglia, L.A. et al., "A Novel Domain within the 55 kd TNF Receptor Signals Cell Death," *Cell* 74:845–853 (1993).

Tewari, M. and V.M. Dixit, "Fas– and Tumor Necrosis Factor–induced Apoptosis Is Inhibited by the Poxvirus crmA Gene Product," *J. Biol. Chem.* 270(7):3255–3260 (Feb. 1995).

Tewari, M. et al., "Yama/CPP32β, a Mammalian Homology of CED–3, Is a CrmA–Inhibitable Protease That Cleaves the Death Substrate Poly(ADP–Ribose) Polymerase," *Cell* 81:801–809 (Jun. 1995).

Thompson, C.B., "Apoptosis in the Pathogenesis and Treatment of Disease," *Science* 267:1456–1462 (Mar. 1995).

Thornberry, N.A. et al., "A novel heterodimeric cysteine protease is required for interleukin–1β processing in monocytes," *Nature* 356:768–774 (1992).

Trauth, B.C. et al., "Monoclonal Antibody–Mediated Tumor Regression by Induction of Apoptosis," *Science* 245:301–305 (1989).

Vaux, D.L. and A. Strasser, "The molecular biology of apoptosis," *Proc. Natl. Acad. Sci. USA* 93:2239–2244 (Mar. 1996).

International Search Report of International Application No. PCT/US97/23548, mailed Apr. 24, 1998.

Database EMBL, Accession No. AA151070, "The WasU–Merck EST Project" (Dec. 1996).

Database EMBL, Accession No. I78285, "The WasU–Merck EST Project" (Apr. 1995).

Database EMBL, Accession No. AA119147, "The WasU––HHMI Mouse EST Project" (Nov. 1996).

NCBI Entrez, GenBank Report, Accession No. T80945, from Hillier, L. et al. ( Mar. 1995), with Revision History.

NCBI Entrez, GenBank Report, Accession No. T81562, from Hillier, L. et al. ( Mar. 1995), with Revision History.

NCBI Entrez, GenBank Report, Accession No. T85205, from Hillier, L. et al. (Mar. 1995), with Revision History.

NCBI Entrez, GenBank Report, Accession No. R37937, from Hillier, L. et al. (May 1995), with Revision History.

NCBI Entrez, GenBank Report, Accession No. N22854, from Hillier, L. et al. (Dec. 1995), with Revision History.

NCBI Entrez, GenBank Report, Accession No. AA304222, from Adams, M.D. et al. (Apr. 1997), with Revision History.

NCBI Entrez, GenBank Report, Accession No. AA362171, from Adams, M.D. et al. (Apr. 1997), with Revision History.

NCBI Entrez, GenBank Report, Accession No. AA150833, from Hillier, L. et al. (May 1997), with Revision History.

NCBI Entrez, GenBank Report, Accession No. AA194018, from Hillier, L. et al. (May 1997), with Revision History.

NCBI Entrez, GenBank Report, Accession No. AA437033, from Hillier, L. et al. (May 1997), with Revision History.

NCBI Entrez, GenBank Report, Accession No. AA442860, from Hillier, L. et al. (Jun. 1997), with Revision History.

NCBI Entrez, GenBank Report, Accession No. AA285065, from NCI–CGAP (Aug. 1997), with Revision History.

NCBI Entrez, GenBank Report, Accession No. AA290955, from NCI–CGAP (Aug. 1997), with Revision History.

NCBI Entrez, GenBank Report, Accession No. AA527472, from NCI–CGAP (Aug 1997), with Revision History.
NCBI Entrez, GenBank Report, Accession No. AA112010, from Hillier, L. et al. (Dec. 1997, with Revision History.
NCBI Entrez, GenBank Report, Accession No. AA074868, from Hillier, L. et al. (Dec. 1997), with Revision History.
NCBI Entrez, GenBank Report, Accession No. AA734783, from Marra, M. et al. (Jan. 1998), with Revision History.
NCBI Entrez, GenBank Report, Accession No. AA745641, from NCI–CGAP (Jan. 1998), with Revision History.
NCBI Entrez, GenBank Report, Accession No. AA626776, from Hillier, L. et al. (Mar. 1998), with Revision History.

```
            10                    30                    50
AACAGTCAGGATTCCGGTTGCAGTTTTTCTCCCCCGCCCCAAAGATACGTGGTTGCAGAC
            70                    90                   110
GGAGAAATGGAGGCCAGAGACAAACAAGTACTCCGCTCACTTCGCCTGGAGCTGGGTGCA
       M  E  A  R  D  K  Q  V  L  R  S  L  R  L  E  L  G  A
           130                   150                   170
GAGGTATTGGTGGAGGGACTGGTTCTTCAGTACCTCTACCAGGAAGGAATCTTGACGGAA
 E  V  L  V  E  G  L  V  L  Q  Y  L  Y  Q  E  G  I  L  T  E
           190                   210                   230
AACCATATTCAAGAAATCAATGCTCAAACCACAGGCCTCCGGAAAACAATGCTCCTGCTG
 N  H  I  Q  E  I  N  A  Q  T  T  G  L  R  K  T  M  L  L  L
           250                   270                   290
GATATCCTACCTTCCAGGGGCCCTAAAGCATTTGATACATTCCTAGATTCCCTACAGGAG
 D  I  L  P  S  R  G  P  K  A  F  D  T  F  L  D  S  L  Q  E
           310                   330                   350
TTTCCCTGGGTCAGGGAGAAGCTGAAGAAGGCAAGGGAAGAGGCCATGACCGACCTGCCT
 F  P  W  V  R  E  K  L  K  K  A  R  E  E  A  M  T  D  L  P
           370                   390                   410
GCAGGTGACAGATTGACTGGGATCCCCTCGCACATCCTCAACAGCTCCCCATCAGACCGG
 A  G  D  R  L  T  G  I  P  S  H  I  L  N  S  S  P  S  D  R
           430                   450                   470
CAGATTAACCAGCTGGCCCAGAGGCTGGGCCCTGAGTGGGAGCCCATGGTGTTGTCTCTG
 Q  I  N  Q  L  A  Q  R  L  G  P  E  W  E  P  M  V  L  S  L
           490                   510                   530
GGACTGTCCCAGACGGATATCTACCGCTGTAAGGCCAACCACCCCCACAACGTGCAGTCG
 G  L  S  Q  T  D  I  Y  R  C  K  A  N  H  P  H  N  V  Q  S
           550                   570                   590
CAGGTGGTGGAGGCCTTCATCCGTTGGCGGCAGCGCTTCGGGAAGCAGGCCACCTTCCAG
 Q  V  V  E  A  F  I  R  W  R  Q  R  F  G  K  Q  A  T  F  Q
           610                   630                   650
AGCCTGCACAACGGGCTGCGGGCTGTGGAGGTGGACCCCTCGCTGCTCCTGCACATGTTG
 S  L  H  N  G  L  R  A  V  E  V  D  P  S  L  L  L  H  M  L
           670                   690                   710
GAGTGATGGTGCCTCCAGCAACCGCTGGGGAGTGTGTCCCTGAGTCATGTGGGCTGAATC
 E  *
           730                   750                   770
CTGACTTTCACTCAGAGCAGGTGGTTTTTTGTGTAGGTTTGTTTTTTATTTTTTGATGATC
           790                   810                   830
TTCAGATGGAAGGAGAAAACAGGGTTTCCACTAGACATTACTTGAAAGGCCAGATTACTC
           850                   870                   890
AGCAGATCTCCCATGTTGGCTCAACAATTCTTTGTTTTTAATTGCTTGAAGATTGCATTG
           910                   930                   950
TTGTAATTGTTCAGTTTTTAAATGTGTAATGGCATTTTAATAGACTAGTAAATCACAGTG
           970                   990                  1010
GTTCCAAATATATACCCATATATATATATATCCATATATATATCTCATGTCATCACATTA
          1030                  1050                  1070
CAGGCAGGTGTCTCATATGTAAAACATTTACCTGAATGTTGTCTGAGGACTGAACTGTGG
          1090                  1110                  1130
ACTTTACTATTCATAATGATAAAATAATAAAATGCGAATTACTATAAAAAAAAAAAAAAA
          1150
AAAAAAAAAAAAAAAAAAAA
```

FIG.1

N-Terminal Domain (NTD)

```
 9  L R S L R L E L G A E V L V E G L V L Q Y L Y Q E G I L T E N H I Q E I N A   N-RAIDD
23  L K K N R V L A K Q L L S E L - L E H L L E K D I T L E M R E L I Q A         N-ICH1
10  L E R N I M M F S S H L K V D E T - L E V L I A K Q V L N S D N G D M I N S   N-CED-3

47  Q T T G L R K T M L L D I L P S R G P X A F D T F L D S L Q E . . . .         N-RAIDD
60  K V G S F S Q N V E L L N L L P K R G P Q A F D A F C E A L R E . . . .       N-ICH1
47  C G T V R E K R R E I V K A V Q R R G D V A F D A F Y D A L R . . . .         N-CED-3
```

FIG.2B

Death Domain (DD)

```
123  L A Q R L G P E W E P M V L S L G - - - - - L S Q T D T Y R C K A N H P H N - V Q S Q V   RAIDD-DD
104  I C D N V G K D W R R L A R Q L K - - - - - V S D T K I D S I E D R Y P R N - L T E R V   FADD-DD
222  F A R S V G L K W R K V G R S L Q R G C R A L R D P A L D S L A Y E Y E R E G L Y E Q A   TRADD-DD
590  I R E N L G K H W K N C A R K L G - - - - - - - - - F T Q S Q I D E I D H D Y E R D G L K E K V   RIP-DD

161  V E A F I R W R Q R F G K Q - A T F Q S L H N G L R A - - - V E V D P S L L . .           RAIDD-DD
142  R E I S L R I W - K N T E K E N A T V A H L V G A L R S C - Q M N L V A D L V . .         FADD-DD
266  F Q L L R R F V Q A E G R R - A T L Q R L V E A L E E N E L T S L A E D L L . .           TRADD-DD
629  Y Q M L Q K W V M R E G I K G A T V G K L L A Q A L H Q C S R I D L L S S L I . .         RIP-DD
```

FIG.2C

RAIDD, A NOVEL DEATH ADAPTOR MOLECULE

This application claims the benefit of the filing date of provisional application Ser. No. 60/033,868 filed on Dec. 20, 1996, which is herein incorporated by reference.

BACKGROUND OF THE INVENTION

1. Field of the Invention

The present invention relates to a novel molecule involved in the process of apoptosis. More specifically, isolated nucleic acid molecules are provided encoding the human RAIDD protein and two splice variants thereof—referred to as RAIDD-SV1 and RAIDD-SV2. RAIDD polypeptides are also provided, as are vectors, host cells and recombinant methods for producing the same. The invention further relates to screening methods for identifying agonists and antagonists of RAIDD activity.

2. Related Art

Apoptosis, or programmed cell death, is a physiological process essential to the normal development and homeostasis of multicellular organisms (Steller, *Science* 267:1445–1449 (1995)). Derangements of apoptosis contribute to the pathogenesis of several human diseases including cancer, neurodegenerative disorders, and acquired immune deficiency syndrome (Thompson, *Science* 267:1456–1462 (1995)).

Apoptotic cell death is a multi-phase process (Vaux and Strasser, *Proc. Natl. Acad. Sci. USA* 93:2239–2244 (1996); Takahashi and Earnshaw, *Curr. Opin. Genet. Dev.* 6:50–55 (1996)). In the first phase cells react to either external or internal stimuli capable of inducing apoptosis followed by transduction of the stimulus to the cell death effector machinery. In the next phase, cell death machinery is activated resulting in the cells undergoing dramatic changes in structure. This last phase is characterized by the activation of both nucleases and proteases.

Two cell surface receptors, CD95 (Fas/APO-1) and TNFR-1, have been shown to trigger apoptosis by their natural ligands or specific agonist antibodies (Baglioni, *Tumor Necrosis Factors*, "The Molecules and their Emerging Role in Medicine," B. Beutler, ed., pp. 425–438 (1992); Itoh et al., *Cell* 66:233–43 (1991); Trauth et al., *Science* 245:301–05 (1989)). Both death receptors are members of the tumor necrosis factor (TNF)/nerve growth factor (NGF) receptor family which also include TNFR-2, low-affinity MGFR, CD40 and CD30, among others (Smith et al., *Science* 248:1019–23 (1990); Tewvari et al., *Cell* 81:801–809 (1995)).

CD95 and TNFR-1 share a region of homology, appropriately designed the "death domain," required to signal apoptosis (Itoh et al., *J. Biol. Chem.* 268:10932–7 (1993); Tartaglia et al., *Cell* 74:845–53 (1993)). This shared "death domain" suggests that both receptors interact with a related set of signal transducing molecules that, until recently, remained unidentified. Using the two-hybrid system, three death domain-containing molecules, TRADD, FADD/MORT1 and RIP, were isolated (Boldin et al., *J. Biol. Chem.* 270:7795–8 (1995); Chinnaiyan et al., *Cell* 81:505–12 (1995); Cleveland et al., *Cell* 81:479–82 (1995); Hsu et al., *Cell* 81:495–504 (1995); Stanger et al., *Cell* 81:513–23 (1995)). Subsequent studies showed that endogenous FADD associates with CD95 in an activation-dependent fashion (Kischkel et al., *EMBO* 14:5579–88 (1995)), while similarly, endogenous TRADD and RIP were found complexed to activated TNFR-1 (Hsu et al., *Cell* 84:299–308 (1996); Hsu et al., *Immunity* 4:387–96 (1996)). It has been postulated that TRADD acts as an adaptor molecule for TNFR-1 (Hsu et al., *Cell* 84:299–308 (1996)), mediating the interaction of TNFR-1 with FADD, while, by contrast, RIP may be involved in NF-KB signaling (Hsu et al., *Immunity* 4:387–96 (1996)). A dominant negative version of FADD (FADD-DN) blocks TNF- and CD95-induced apoptosis, suggesting that FADD functions as the common signaling conduit for cytokine-mediated cell death (Chinnaiyan et al., *J. Biol. Chem.* 271:4961–65 (1996); Hsu et al., *Cell* 84:299–308 (1996)).

Overexpression of several proteins containing death domains has been shown to result in the induction of apoptotic cell death in the absence of an apoptotic induction stimulus (Vaux and Strasser, supra). Further, a number of viruses have been found to encode specific inhibitors of apoptosis, suggesting a role for apoptosis in antiviral defense.

Overexpression of TRADD induces both apoptosis and NF-kB activation-two of the most important activities signaled by TNFR-1 (Hsu et al., *Cell* 81:495–504 (1995)). Upon oligomerization of TNFR-1 by trimeric TNF, TRADD is recruited to the receptor signaling complex (Hsu et al., *Cell* 84:299–308 (1996)). TRADD can then recruit the following signal transducing molecules: 1) TRAF2, a TNFR-2- and CD40- associated molecule (Rothe et al., *Cell* 78:681–92 (1994); Rothe et al., *Science* 269:1424–1427 (1995)), that mediates NF-KB activation, 2) RIP, originally identified as a Fas/APO-1-interacting protein by two-hybrid analysis (Stanger et al., *Cell* 81:513–23 (1995)), that mediates NF-kB activation and apoptosis (Hsu et al., *Immunity* 4:387–96 (1996)), and 3) FADD, a Fas/APO-1-associated molecule, that mediates apoptosis (Chinnaiyan et a., *Cell* 81:505–12 (1995); M. P. Boldin et al., *J. Biol. Chem.* 270:7795–8 (1995); F. C. Kischkel et al., *EMBO* 14:5579–5588 (1995)).

Studies have demonstrated that FADD can recruit the ICE/CED-3-like protease FLICE to the Fas/APO-1 death inducing signaling complex (Muzio et al., *Cell* 85:817–827 (1996); Boldin et al., *Cell* 85:803–815 (1996)).

The first evidence for the involvement of ICE-like proteases in CD95- and TNFR-1 signaling came with the discovery that the poxvirus gene product CrmA blocks cell death triggered by both receptors (Enari et al., *Nature* 375:78–81 (1995); Los et al., *Nature* 375:81–3 (1995); Tewari et al., *J. Biol. Chem.* 270:3255–60 (1995)). In vitro, the serpin CrmA interacts only with the active forms of ICE and ICE-like proteases (Ray et al., *Cell* 69:597–604 (1992); Tewari et al., *Cell* 81:801–09 (1995)). Yama and ICE-LAP3, two of the ICE-like enzymes most related to CED-3, are expressed as zymogens that are proteolytically activated upon ligation of CD95 or TNFR-1 (Chinnaiyan et al.,*J. Biol. Chem.* 271:4961–65 (1996); Duan et a., *J. Biol. Chem.* 271:35013–35 (1996)). However, both Yama and ICE-LAP3 remained a proenzymes in anti-CD95 treated CrmA-expressing cells, suggesting that CrmA inhibits an ICE-like protease upstream of Yama and ICE-LAP3 (Chinnaiyan et al., *J. Biol. Chem.* 271:4961–65 (1996)).

Phylogenetic analysis of the ICE/ced-3 gene family revealed three subfamilies (Chinnaiyan et al., *Current Biology* 6:555–62 (1996); Duan et al., *J. Biol. Chem.* 271:35013–35 (1996)). Yama, ICE-LAP3, and Mch2 are closely related to *C. elegans* Ced-3 and comprise the Ced-3 subfamily. ICE and the ICE-related genes, ICE rel II, and ICE rel III form the ICE subfamily, while ICH-1 and its mouse homologue, NEDD-2 form the NEDD-2 subfamily.

Based on similarities with the structural prototype interleukin-1b converting enzyme, ICE/Ced-3 family members are synthesized as zymogens that are capable of being processed to form active heterodimeric enzymes (Thornberry et al., Nature 356:768–74 (1992)).

SUMMARY OF THE INVENTION

The present invention provides isolated nucleic acid molecules comprising a polynucleotide encoding the RAIDD polypeptide having the amino acid sequence shown in FIG. 1 (SEQ ID NO:2) or the amino acid sequence encoded by the cDNA clone deposited as ATCC Deposit Number 97824 on Dec. 13, 1996.

The present invention further provides isolated nucleic acid molecules comprising a polynucleotide encoding RAIDD polypeptide splice variants—RAIDD-SV1 and RAIDD-SV2.

The present invention also relates to recombinant vectors, which include the isolated nucleic acid molecules of the present invention, and to host cells containing the recombinant vectors, as well as to methods of making such vectors and host cells and for using them for production of RAIDD polypeptides or peptides by recombinant techniques.

The invention further provides an isolated RAIDD polypeptide, and splice variants thereof, having an amino acid sequence encoded by a polynucleotide described herein.

The present invention also provides a screening method for identifying agonists and antagonists of RAIDD induced cell death, which involves contacting cells which express the RAIDD protein with a candidate molecule and comparing the level of RAIDD induced cell death to a standard level, the standard being assayed when contact is made in absence of the candidate molecule; whereby, an increase in RAIDD induced cell death in comparison to the standard indicates that the compound is an agonist and a decrease in RAIDD induced cell death in comparison to the standard indicates that the compound is an antagonist.

The present invention further provides a screening method for identifying compounds capable of interaction with the RAIDD polypeptides of the present invention, which involves contacting a RAIDD polypeptide with a candidate molecule and measuring whether the candidate molecule interacts with the RAIDD polypeptide.

BRIEF DESCRIPTION OF THE FIGURES

FIG. 1 shows the nucleotide (SEQ ID NO:1) and deduced amino acid (SEQ ID NO:2) sequences of RAIDD. The protein has a deduced molecular weight of about 22 kDa. The amino acid residues which are underlined and italicized make up the RAIDD-SV1 splice variant. The amino acid residues which are italicized make up the RAIDD-SV2 splice variant FIGS. 2A–2C show a schematic representation of the RAIDD protein and a comparison of regions of homology between the functional domains of the RAIDD polypeptide and known proteins. FIG. 2A shows a schematic representation of the domains of the RAIDD polypeptide. FIG. 2B shows a comparison between amino acid residues 9–78 of the RAIDD protein and portions of both ICH-1 (SEQ ID NO:3) and the C. elegans death protease CED-3 (SEQ ID NO:4). FIG. 2C shows a comparison between amino acid residues 123–194 of the RAIDD protein and the death domain containing regions of FADD (SEQ ID NO:5), TRADD (SEQ ID NO:6), and RIP (SEQ ID NO:7). Identical amino acids in FIG. 2B and FIG. 2C are boxed. Numbers in FIGS. 2A–2C represent amino acid residues which correspond to amino acids residues shown in SEQ ID NO:2.

DETAILED DESCRIPTION

Figure 2A:
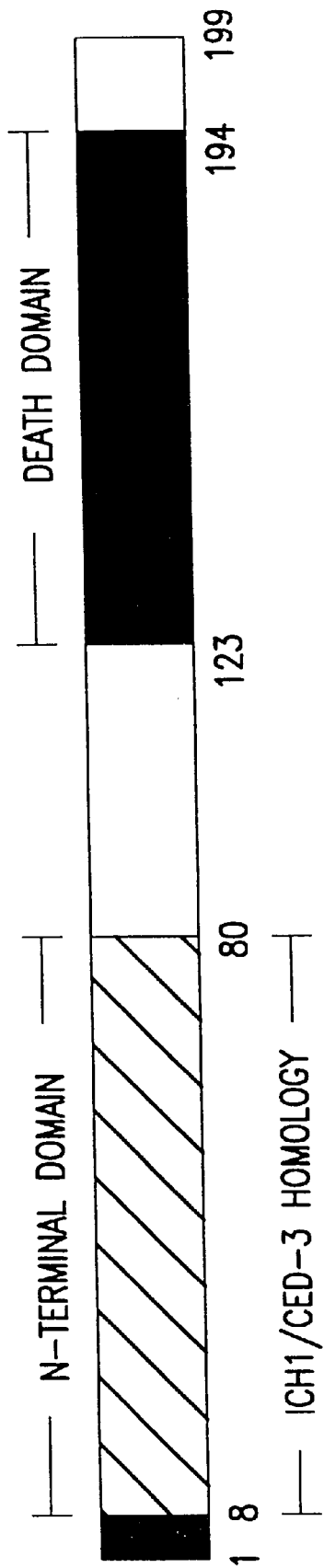
Figure 3:
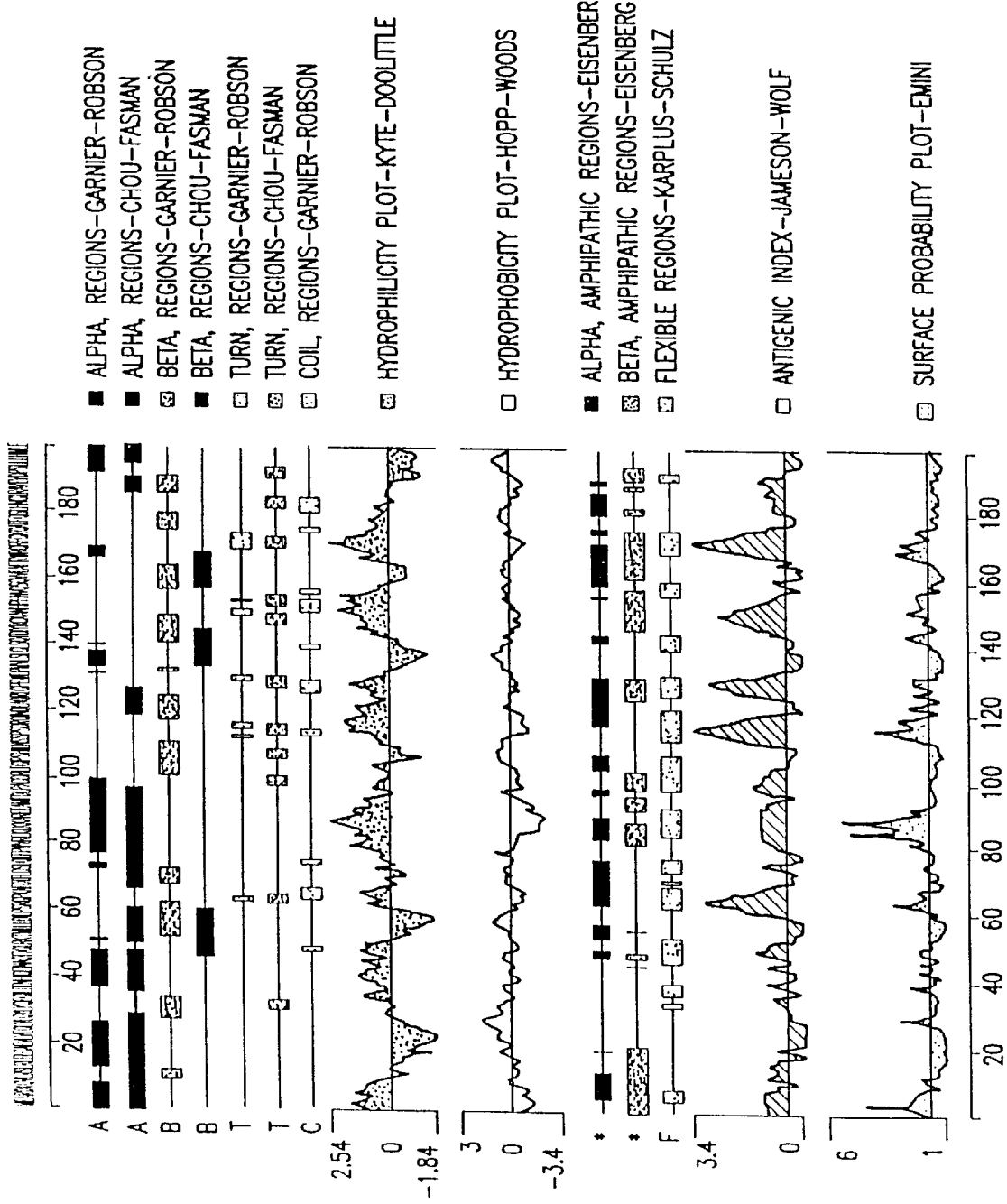
FIG. 3 shows an analysis of the RAIDD amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues about 61 to about 71, about 112 to about 134, about 144 to about 159, and about 168 to about 178, in FIG. 1 (SEQ ID NO:2) correspond to the shown highly antigenic regions of the RAIDD protein.

The present invention provides isolated nucleic acid molecules comprising a polynucleotide encoding a RAIDD polypeptide having the amino acid sequence shown in SEQ ID NO:2, which was determined by sequencing a cloned cDNA. Regions of the RAIDD proteins of the present invention share sequence homology with human ICH-1 (SEQ ID NO:3), CED-3 of C. elegans (SEQ ID NO:4), FADD (SEQ ID NO:5), TRADD (SEQ ID NO:6), and RIP (SEQ ID NO:7) (see FIGS. 2B and 2C). The nucleotide sequence shown in SEQ ID NO:1 was obtained by sequencing the HSDME38XX clone, which was deposited on Dec. 13, 1996 at the American Type Culture Collection, 10801 University Blvd., Manassas, Va. 20110-2209, USA and given accession number 97824. The deposited clone is inserted in the pBluescript SK(−) plasmid (Stratagene, LaJolla, Calif.) using the EcoRI and XhoI restriction endonuclease cleavage sites.

Splice variants of the RAIDD protein, referred to herein as RAIDD-SV1 and RAIDD-SV2, have been identified and included in the present invention. As used herein the phrase "splice variant" refers to cDNA molecules produced from RNA molecules initially transcribed from the same genomic DNA sequence which have undergone alternative RNA splicing. Alternative RNA splicing occurs when a primary RNA transcript undergoes splicing, generally for the removal of introns, which results in the production of more than one mRNA molecule each of which may encode different amino acid sequences. The term "splice variant" also refers to the proteins encoded by the above cDNA molecules.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in SEQ ID NO:1, a nucleic acid molecule of the present invention encoding a RAIDD polypeptide may be obtained using standard cloning and screening procedures, such as those for cloning cDNAs using mRNA as starting material. Illustrative of the invention, the nucleic acid molecule described in SEQ ID NO:1 was discovered in human K562 cell line cDNA library. As noted in Example 4, the RAIDD gene is constitutively expressed in all adult and fetal tissues examined with substantial expression in each. These tissues include heart, testis, skeletal muscle, liver and kidney. The determined nucleotide sequence of the RAIDD cDNA of SEQ ID NO:1 contains an open reading frame encoding a protein of about 199 amino acid residues and a deduced molecular weight of about 22 kDa The amino acid sequence of the predicted full length RAIDD polypeptide is shown in SEQ ID NO:2. The N-terminal portion of the RAIDD protein shown in SEQ ID NO:2 (amino acid residues from about 8 to about 80) is about 40% identical and about 50% similar to the pro-domain of the human cysteine protease ICH-1 (amino acid residues 23 to 91 in FIG. 2B) (SEQ ID NO:3) and about 35% identical and about 40% similar to the pro-domain of the C. elegans death protease CED-3 (amino acid residues 10 to 77 in FIG. 2B) (SEQ ID NO:4). In addition, the C-terminal portion of the RAIDD protein shown in SEQ ID NO:2 (amino acids residues from about 123 to about 194) is about 25% identical and about 35% similar to the death domain region of the human FADD protein (amino acid residues 104 to 177 in FIG. 2C) (SEQ ID NO:5), about 25% identical and about 35% similar to the death domain region of the human TRADD protein (amino acid residues 222 to 302 in FIG. 2C) (SEQ ID NO:6), and about 30% identical and about 30% similar to the death domain region of the human RIP protein (amino acid residues 590 to 666 in FIG. 2C) (SEQ ID NO:7).

As one of ordinary skill would appreciate, due to the possibilities of sequencing errors, the predicted RAIDD polypeptide encoded by the deposited cDNA comprises about 199 amino acids, but may be anywhere in the range of about 189 to about 209 amino acids.

Splice variants of RAIDD have also been identified. These splice variants include RAIDD-SV1 and RAIDD-SV2. RAIDD-SV1 comprises essentially the linker region and death domain of the full-length RAIDD polypeptide (amino acid residues from about 99 to about 199 shown in SEQ ID NO:2). RAIDD-SV2 comprises essentially only the death domain of the full-length RAIDD polypeptide (amino acid residues from about 111 to about 199 shown in SEQ ID NO:2).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising the open reading frame (ORF) shown in SEQ ID NO:1; DNA molecules comprising the ORF shown in SEQ ID NO:1 without the ATG codon encoding the N terminal methionine residue; DNA molecules encoding amino acid residues from about 99 to about 199 in SEQ ID NO:2; DNA molecules encoding amino acid residues from about 118 to about 199 in SEQ ID NO:2; and DNA molecules which comprise a sequence substantially different from those described above but which, due to the degeneracy of the genetic code, still encode the RAIDD protein or a splice variant thereof. Of course, the genetic code is well known in the art Thus, it would be routine for one skilled in the art to generate such degenerate variants.

In another aspect, the invention provides isolated nucleic acid molecules encoding the RAIDD polypeptide having an amino acid sequence encoded by the cDNA clone contained in the plasmid deposited as ATCC Deposit No. 97824 on Dec. 13, 1996. The invention further provides an isolated nucleic acid molecule having the nucleotide sequence shown in SEQ ID NO:1 or the nucleotide sequence of the RAIDD cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the RAIDD gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in SEQ ID NO:1 is intended fragments at least about 15 nt, and more preferably at least about 20 nt, still more preferably at least about 30 nt, and even more preferably, at least about 40 nt in length which are useful as diagnostic probes and primers as discussed herein. Of course larger DNA fragments 50, 100, 150, 200, 250, 300, 350, 400, 450, 500, 550, 600, 650, 700, 750, 800, 850, 900, 950, 1000, 1050, 1100, or 1125 nt in length of the sequence shown in SEQ ID NO:1 are also useful according to the present invention as are fragments corresponding to most, if not all, of the nucleotide sequence of the cDNA clone contained in the plasmid deposited as ATCC Deposit No. 97824 or as shown in SEQ ID NO:1. By a fragment at least 20 nt in length, for example, is intended fragments which include 20 or more contiguous bases from the nucleotide sequence of the deposited cDNA or the nucleotide sequence as shown in SEQ ID NO:1.

Preferred nucleic acid fragments of the present invention include nucleic acid molecules encoding epitope-bearing portions of the RAIDD protein. In particular, such nucleic acid fragments of the present invention include nucleic acid molecules encoding: a polypeptide comprising amino acid residues from about 61 to about 71 in SEQ ID NO:2; a polypeptide comprising amino acid residues from about 112 to about 134 in SEQ ID NO:2; a polypeptide comprising amino acid residues from about 144 to about 159 in SEQ ID NO:2; and a polypeptide comprising amino acid residues from about 168 to about 178 in SEQ ID NO:2. The inventors have determined that the above polypeptide fragments are antigenic regions of the RAIDD protein. Methods for determining other such epitope-bearing portions of the RAIDD protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97824. By "stringent hybridization conditions" is intended overnight incubation at 42° C. in a solution comprising: 50% formamide, 5× SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1× SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1). Of course, a polynucleotide which hybridizes only to a poly A sequence (such as the 3' terminal poly(A) tract of the RAIDD cDNA shown in SEQ ID NO:1), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a RAIDD polypeptide may include, but are not limited to those encoding the amino acid sequence of the mature polypeptide, by itself; the coding sequence for the mature polypeptide and additional sequences, such as those encoding an amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example— ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767 (1984). As discussed below, other such fusion proteins include the RAIDD protein fused to Fc at the N- or C-terminus.

The present invention further relates to variants of the nucleic acid molecules of the present invention, which encode portions, analogs or derivatives of a RAIDD protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the RAIDD protein or portions thereof. Also especially preferred in this regard are conservative substitutions.

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the RAIDD polypeptide having the amino acid sequence in SEQ ID NO:2; (b) a nucleotide sequence encoding the RAIDD polypeptide having the amino sequence shown in SEQ ID NO:2 but lacking the N-terminal methionine (amino acid residues 2 to 199 in SEQ ID NO:2); (c) a nucleotide sequence encoding the RAIDD-SV1 protein (amino acid residues from about 99 to about 199 in SEQ ID NO:2); (d) a nucleotide sequence encoding the RAIDD-SV2 protein (amino acid residues from about 118 to about 199 in SEQ ID NO:2); (e) a nucleotide sequence encoding a RAIDD cysteine protease domain (amino acid residues from about 8 to about 80 in SEQ ID NO:2); (f) a nucleotide sequence encoding a RAIDD death domain (amino acid residues from about 123 to about 194 in SEQ ID NO:2); (g) a nucleotide sequence encoding the RAIDD polypeptide having the amino acid sequence encoded by the cDNA clone contained in ATCC Deposit No. 97824; or (h) a nucleotide sequence complementary to any of the nucleotide sequences in (a), (b), (c), (d), (e), (f) or (g).

By a polynucleotide having a nucleotide sequence at least, for example, 95% "identical" to a reference nucleotide sequence encoding a RAIDD polypeptide is intended that the nucleotide sequence of the polynucleotide is identical to the reference sequence except that the polynucleotide sequence may include up to five point mutations per each 100 nucleotides of the reference nucleotide sequence encoding the RAIDD polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to those described above can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to those described above irrespective of whether they encode a polypeptide having RAIDD activity. This is because even where a particular nucleic acid molecule does not encode a polypeptide having RAIDD activity, one of skill in the art would still know how to use the nucleic acid molecule, for instance, as a hybridization probe or a polymerase chain reaction (PCR) primer. Uses of the nucleic acid molecules of the present invention that do not encode a polypeptide having RAIDD activity include, inter alia, (1) isolating the RAIDD gene, or splice or allelic variants thereof, in a cDNA library; (2) in situ hybridization (e.g., "FISH") to metaphase chromosomal spreads to provide precise chromosomal location of the RAIDD gene, as described in Verma et al., *Human Chromosomes: A Manual of Basic Techniques*, Pergamon Press, New York (1988); and (3) Northern Blot analysis for detecting RAIDD mRNA expression in specific tissues.

Preferred, however, are nucleic acid molecules having sequences at least 95%, 96%, 97%, 98% or 99% identical to the nucleic acid sequence shown in SEQ ID NO:1 or to the nucleic acid sequence of the deposited cDNA which do, in fact, encode a polypeptide having RAIDD protein activity. By "a polypeptide having RAIDD activity" is intended polypeptides exhibiting activity similar, but not necessarily identical, to an activity of the RAIDD protein of the invention (either the full-length protein or splice variants thereof), as measured in a particular biological assay. For example, RAIDD protein activity can be measured using either the ICH-1 binding or apoptosis assay described in Example 4.

Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence of the deposited cDNA or the nucleic acid sequence shown in SEQ ID NO:1 will encode a polypeptide "having RAIDD protein activity." In fact, since degenerate variants of these nucleotide sequences all encode the same polypeptide, this will be clear to the skilled artisan even without performing the above described comparison assays. It will be further recognized in the art that, for such nucleic acid molecules that are not degenerate variants, a reasonable number will also encode a polypeptide having RAIDD protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of RAIDD polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDRS40, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins have been fused with Fc portions for the purpose of high-throughput screening assays to identify molecules with antagonistic activity. One example is the hIL-5 receptor which has been used to identify antagonists of hIL-5. See, D. Bennett et al., *Jour. of Molecular Recognition*, 8:52–58 (1995) and K. Johanson et al., *Jour. Biol. Chem.*, 270:9459–9471 (1995).

The RAIDD protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated.

In addition, polypeptides of the invention may also include an initial modified methionine residue, in some cases as a result of host-mediated processes.

RAIDD Polypeptides and Fragments

The invention further provides an isolated RAIDD polypeptide having the amino acid sequence encoded by the deposited cDNA, or the amino acid sequence in SEQ ID NO:2, or a peptide or polypeptide comprising a portion of the above polypeptides.

It will be recognized in the art that some amino acid sequences of the RAIDD polypeptide can be varied without significant effect of the structure or function of the protein. If such differences in sequence are contemplated, it should be remembered that there will be critical areas on the protein which determine activity.

Thus, the invention flirter includes variations of the RAIDD polypeptides of the present invention which show substantial RAIDD polypeptide activity or which include regions of a RAIDD protein such as the protein portions discussed below. Such mutants include deletions, insertions, inversions, repeats, and type substitutions. As indicated above, guidance concerning which amino acid changes are likely to be phenotypically silent can be found in Bowie, J. U. et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the RAIDD protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al., *Crit. Rev. Therapeutic Drug Carrier Systems* 10:307–377 (1993)).

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |

TABLE 1-continued

Conservative Amino Acid Substitutions.

| | |
|---|---|
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above and below. Generally speaking, the number of substitutions for any given RAIDD polypeptide, or mutant thereof, will not be more than 50, 40, 30, 20, 10, 5, or 3, depending on the objective.

Amino acids in a RAIDD protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as the ability to bind ICH-1 or CED-3 or the ability to induce apoptosis when overexpressed. Sites that are critical for RAIDD-ligand interaction can also be determined by structural analysis such as crystallization, nuclear magnetic resonance or photoaffinity labeling (Smith et al., *J. Mol. Biol.* 224:899–904 (1992) and de Vos et al., *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of a RAIDD polypeptide described herein can be substantially purified by the one-step method described in Smith and Johnson, *Gene* 67:3140 (1988).

The polypeptides of the present invention include the polypeptide encoded by the deposited cDNA, a polypeptide comprising amino acids from about 1 to about 199 in SEQ ID NO:2; a polypeptide comprising amino acids from about 2 to about 199 in SEQ ID NO:2; a polypeptide comprising amino acids from about 8 to about 80 in SEQ ID NO:2 ; a polypeptide comprising amino acids from about 99 to about 199 in SEQ ID NO:2 ; a polypeptide comprising amino acids from about 118 to about 199 in SEQ ID NO:2; a polypeptide comprising amino acids from about 123 to about 194 in SEQ ID NO:2; as well as polypeptides which are at least 95% identical, more preferably at least 96% identical, still more preferably at least 97%, 98% or 99% identical to those described above and also include portions of such polypeptides with at least 30 amino acids and more preferably at least 50 amino acids.

By a polypeptide having an amino acid sequence at least, for example, 95% "identical" to a reference amino acid sequence of a RAIDD polypeptide is intended that the amino acid sequence of the polypeptide is identical to the reference sequence except that the polypeptide sequence may include up to five amino acid alterations per each 100 amino acids of the reference amino acid of the RAIDD polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:2 or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptides of the present invention could be used as molecular weight markers on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe et al., Antibodies that react with predetermined sites on proteins. *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about at least about 15 to about 30 amino acids contained within the amino acid sequence of a polypeptide of the invention.

Non-limiting examples of antigenic polypeptides or peptides that can be used to generate RAIDD-specific antibodies include: a polypeptide comprising amino acid residues from about 61 to about 71 in SEQ ID NO:2; a polypeptide comprising amino acid residues from about 112 to about 134 in SEQ ID NO:2; a polypeptide comprising amino acid residues from about 144 to about 159 in SEQ ID NO:2; and a polypeptide comprising amino acid residues from about 168 to about 178 in SEQ ID NO:2. As indicated above, the inventors have determined that the above polypeptide fragments are antigenic regions of the RAIDD protein shown in SEQ ID NO:2.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al., (1986).

As one of skill in the art will appreciate, the RAIDD polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than monomeric RAIDD proteins or protein fragments alone (Fountoulakis et al., *J. Biochem* 270:3958–3964 (1995)).

Agonists and Antagonists of RAIDD Polypeptide Function

In one aspect, the present invention is directed to a method for identifying molecules capable of inhibiting or enhancing RAIDD induced cell death. The method involves contacting cells which express a RAIDD polypeptide of the present invention with a candidate molecule, measuring the level of RAIDD induced cell death, and comparing the level of cell death to a standard level of RAIDD induced cell death, wherein the standard level of RAIDD induced cell death is assayed using cells expressing a RAIDD polypeptide in absence of the candidate molecule. According to this method, an increased level of RAIDD induced cell death in comparison to the standard indicates that the candidate molecule is an agonist and a decreased level of RAIDD induced cell death in comparison to the standard indicates that the candidate molecule is an antagonist.

By "RAIDD induced cell death" is intended cell death induced by a pathway involving the RAIDD polypeptide. Methods for measuring RAIDD induced cell death include the RAIDD induced cell death/apoptotic assays described in Example 4. By a "candidate molecule" is intended any naturally occurring or synthetic compound which is screened by the method of the present invention for agonistic or antagonistic activity with respect to an activity of a RAIDD polypeptide of the present invention (e.g., induction of RAIDD induced cell death and the ability to bind cellular ligands such as RIP and ICH-1). A "candidate molecule" is also intended to refer to any molecule which is screened for binding to a RAIDD polypeptide of the present invention. By "binding to a RAIDD polypeptide" is intended an association between a RAIDD polypeptide and the candidate molecule which results from an attractive molecular interaction. By "agonist" is intended naturally occurring and synthetic compounds capable of enhancing or potentiating an activity of a RAIDD polypeptide of the present invention. By "antagonist" is intended naturally occurring and synthetic compounds capable of inhibiting an activity of a RAIDD polypeptide. Whether a candidate "agonist" or "antagonist" of the present invention can enhance or inhibit a RAIDD activity can be determined using art-known assays and those assays described herein.

In a preferred embodiment, cells which express a RAIDD polypeptide via an expression construct are used for the identification of antagonists and agonists of RAIDD activity. In this embodiment, the candidate molecule is either added exogenously or is produced endogenously by the transfected cells. Measurement of an increased or decreased level of RAIDD induced cell death is made by comparing the percentage of cells in contact with the candidate molecule which undergo cell death to those of a standard in which the cells are not in contact with the candidate molecule. As described in Example 4, expression of β-galactosidase via a reporter construct may be used to identify cells which have undergone apoptotic demise.

In an additional embodiments, cells are transfected with one or more expression constructs which express both RAIDD and the candidate molecule. As above, the percentage of cells undergoing apoptotic cells death is scored as in Example 4.

As noted in Example 4, several inhibitors of RAIDD induced cell death have been identified using the method disclosed herein. These include the ICE peptide inhibitor z-VAD-fmk, CrmA and catalytically inactive ICH-1. Other potential agonists and antagonists of the present invention include molecules of the RAIDD induced cell death pathway which interact with a RAIDD polypeptide.

Further antagonist according to the present invention include both the RAIDD death and protease domains and fragments of each. Such forms of the RAIDD protein, which may be naturally occurring or synthetic, antagonize RAIDD polypeptide mediated activity by competing for binding to cellular ligands of RAIDD. Thus, such antagonists include fragments of the RAIDD polypeptide containing ligand binding domains.

RAIDD polypeptide antagonists also include small molecules which bind to and occupy active regions of the RAIDD polypeptides thereby making the polypeptide inaccessible to ligands which bind thereto such that normal biological activity is prevented. Examples of small molecules include but are not limited to nucleotide sequences and small peptides or peptide-like molecules. Such molecules may be produced and screened for activity by a variety of methods (e.g., Light and Lerner, *Bioorganic & Medicinal Chemistry* 3(7):955–967 (1995); Cheng et al., *Gene* 171:1–8 (1996); Gates et al., *J. Mol. Biol.* 255:373–386 (1996)).

Other assays for identifying potential antagonists and agonists of RAIDD induced cell death are described in the art and in Example 4. These assays include in vitro and in vivo binding assays for the identification of molecules which interact with the RAIDD polypeptides of the present invention, as described in Example 4, and the yeast two-hybrid system (Fields and Song, *Nature* 340:245–246 (1989)). These method involves contacting the RAIDD polypeptide of the present invention with a candidate molecule and determining whether the molecules interact Thus, in an additional aspect, the present invention is directed to a method for identifying molecules capable of binding the RAIDD polypeptides.

In a preferred embodiment, a RAIDD polypeptide is produced with a histidine tag allowing for affinity purification using nickel-nitrilo-tri-acetic acid ("Ni-NTA") affinity resin. The His-RAIDD polypeptide is purified and incubated with a candidate molecule which has been radiolabelled. The RAIDD polypeptide is then re-purified under non-denaturing conditions and a determination is made as to whether the candidate molecule co-purifies with the RAIDD polypeptide. When the candidate molecule is a protein, this determination can be made by boiling the putative RAIDD-candidate molecule conjugate in an aqueous solution with SDS followed by SDS-PAGE and autoradiography. Candidate molecules which interact with the RAIDD polypeptide are potential agonists and antagonist of RAIDD activity.

Having generally described the invention, the same will be more readily understood by reference to the following examples, which are provided by way of illustration and are not intended as limiting.

EXAMPLES

Example 1

Expression and Purification of RAIDD in *E. coli*

The bacterial expression vector pQE9 (pD10) is used for bacterial expression in this example. (QIAGEN, Inc., 9259 Eton Avenue, Chatsworth, Calif., 91311). pQE9 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6× His tag") covalently linked to the amino terminus of that polypeptide.

The DNA sequence encoding the desired portion of the RAIDD protein is amplified from the deposited cDNA clone using PCR oligonucleotide primers which anneal to the amino terminal sequences of the desired portion of the RAIDD protein and to sequences in the deposited construct 3' to the cDNA coding sequence. Additional nucleotides containing restriction sites to facilitate cloning in the pQE9 vector are added to the 5' and 3' primer sequences, respectively.

For cloning the protein, suitable 5' primers would be apparent to those skilled in the art. In a preferred embodiment, a primer at least 15 to 20 nucleotides in length is used containing one or more appropriately located restriction sites followed by at least 10 nucleotides complementary to the amino terminal sequence encoding the RAIDD protein shown in SEQ ID NO:1. One of ordinary skill in the art would appreciate, of course, that the point in the protein coding sequence where the 5' primer begins may be varied to amplify a DNA segment encoding any desired portion or domain of the complete RAIDD protein.

Suitable 3' primers would also be apparent to those skilled in the art and include those preferably at least 15 to 20 nucleotides in length, containing one or more appropriately located restriction sites, followed by at least 10 nucleotides complementary to either the carboxy terminal coding region or the non-coding region of the sequence shown in SEQ ID NO:1.

The amplified RAIDD DNA fragment and the vector pQE9 are digested with appropriate restriction enzymes to generate suitable "sticky" ends and the digested DNA molecules are then ligated together. Insertion of the RAIDD DNA into the restricted pQE9 vector can be done to place the RAIDD protein coding region downstream from the IPTG-inducible promoter and in-frame with an initiating AUG and the six histidine codons.

The ligation mixture is transformed into competent *E. coli* cells using standard procedures such as those described in Sambrook et al., *Molecular Cloning: a Laboratory Manual*, 2nd Ed; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan$^r$"), is used in carrying out the illustrative example described herein. This strain, which is only one of many that are suitable for expressing RAIDD protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nr ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6 M guanidine-HCl, pH 8. The cell debris is removed by centrifugation, and the supernatant containing the RAIDD is loaded onto a nickel-nitrilo-tri-acetic acid ("NiNTA") affinity resin column (available from QIAGEN, Inc., supra). Proteins with a 6× His tag bind to the NI-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the RAIDD is eluted with 6 M guanidine-HCl, pH 5.

The purified protein is then renatured by dialyzing it against phosphate buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6 M-1 M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM imidazole. Imidazole is removed by a final dialyzing step against PBS or 50 mM sodium acetate pH 6 buffer plus 200 mM NaCl. The purified protein is stored at 4° C. or frozen at −80° C.

Alternatively, a procedure similar to that described above may be employed except that the bacterial expression vector pQE60 (QIAGEN, Inc., 9259 Eton Avenue, Chatsworth, Calif., 91311) is used. The use of suitable primers with this vector will result in the covalent linkage of a 6× His tag to the carboxyl terminus of the expressed polypeptide. Similarly, suitable vectors and primers may be used which will result in the expression of a RAIDD polypeptide without any His tag.

Example 2

Cloning and Expression of RAIDD protein in a Baculovirus Expression System

In this illustrative example, the plasmid shuttle vector pA2 GP is used to insert the cloned DNA encoding the protein into a baculovirus to express the RAIDD protein, using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding the RAIDD protein in the deposited clone, is amplified using PCR oligonucleotide primers corresponding to the 5' and 3' sequences of the gene.

Suitable primers for cloning the RAIDD protein can be designed as described above in Example 1.

The amplified fragment is isolated from a 1% agarose gel using a commercially available kit ("Geneclean," BIO 101 Inc., La Jolla, Calif.). The fragment then is digested with the appropriate restriction enzymes and again is purified on a 1% agarose gel. This fragment is designated herein "F1".

The plasmid is also digested with the appropriate restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the human RAIDD gene using the PCR method, in which one of the primers that is used to amplify the gene and the second primer is from well within the vector so that only those bacterial colonies containing the RAIDD gene fragment will show amplification of the DNA. The sequence of the cloned fragment is confirmed by DNA sequencing. This plasmid is designated herein pBacRAIDD.

Five $\mu$g of the plasmid pBacRAIDD is co-transfected with 1.0 $\mu$g of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). 1 $\mu$g of BaculoGold™ virus DNA and 5 $\mu$g of the plasmid pBacRAIDD are mixed in a sterile well of a microtiter plate containing 50 $\mu$l of serum-free Grace's medium (Life Technologies Inc., Gaithersburg, Md.). Afterwards, 10 $\mu$l Lipofectin plus 90 $\mu$l Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 $\mu$i of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-RAIDD.

To verify the expression of the RAIDD gene, Sf9 cells are grown in Grace's medium supplemented with 10% heat inactivated FBS. The cells are infected with the recombinant baculovirus V-RAIDD at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 $\mu$Ci of $^{35}$S-methionine and 5 $\mu$Ci $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 3

Cloning and Expression of RAIDD in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human HeLa 293, H9 and Jurkat cells, mouse NIH3T3 and C127 cells, Cos 1, Cos 7 and CV 1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expressions in COS Cells

The expression plasmid, pRAIDD HA, is made by cloning a cDNA encoding RAIDD into the expression vector pcDNAIIAmp or pcDNAHI (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the RAIDD protein is cloned into the polylinker region of the vector so that recombinant protein expression is directed by the CMV promoter. The plasmid construction strategy is as follows. The RAIDD cDNA of the deposited clone is amplified using primers that contain convenient restriction sites, much as described in Example 1 above for construction of vectors for expression of RAIDD in *E. coli* Suitable primers would be apparent to one skilled in the art. In a preferred embodiment such primers are at least 15 to 20 nucleotides in length and have the following characteristics. The 5' primer contains one or more appropriately located restriction sites, a Kozak sequence, an AUG start codon and 5 to 10 codons of the 5' coding region of the RAIDD sequence shown in SEQ ID NO:1. The 3' primer contains one or more appropriately located restriction sites, a stop codon, and 15 to 20 bp of either 3' coding or noncoding sequence shown in SEQ ID NO:1. These primers may be designed such that any region or domain of the RAIDD protein is cloned.

The PCR amplified DNA fragment and the vector, pcDNAI/Amp, are digested with appropriate restriction enzymes and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the RAIDD-encoding fragment.

For expression of recombinant RAIDD, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of RAIDD by the vector.

Expression of the RAIDD-HA fusion protein is detected by radiolabeling and immunoprecipitation, using methods described in, for example Harlow et al., *Antibodies: A Laboratory Manual,* 2nd Ed; Cold Spring Harbor Laboratory Press, Cold Spring Harbor, N.Y. (1988). To this end, two days after transfection, the cells are labeled by incubation in media containing $^{37}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al., cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expressions in CHO Cells

The vector pC4 is used for the expression of RAIDD protein. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta,* 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the RAIDD in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the appropriate restriction enzyme(s) and then dephosphorylated using calf intestinal phosphatase by procedures known in the art. The vector is then isolated from a 1% agarose gel.

The DNA sequence encoding the complete RAIDD protein is amplified using PCR oligonucleotide primers corresponding to the 5' and 3' sequences of the gene. Suitable primers would be apparent to one skilled in the art Such primers would be at least 15 to 20 nucleotides in length. Preferably, suitable 5' primers would contain one or more appropriately located restriction sites followed by an efficient signal for initiation of translation in eukaryotes, as described by Kozak, M., *J. Mol. Biol.* 196:947–950 (1987), and 15 to 20 bases of the coding sequence of the RAIDD shown in SEQ ID NO:1. Similarly, suitable 3' primers would contain one or more appropriately located restriction sites followed by 15 to 20 nucleotides complementary to the non-translated region of the RAIDD gene shown in SEQ ID NO:1. These primers may be designed such that any region or domain of the RAIDD protein is cloned.

The amplified fragment is digested with the appropriate restriction enzyme(s) and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofectin (Felgner et at., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reverse phase HPLC analysis.

Example 4

RAIDD, A Novel Death Adaptor Molecule

A sequence (I.M.A.G.E. Consortium CloneID 109053) was identified in the NCBI GenBank™ EST database as having statistically significant homology (p<0.00 1) to the prodomain of the human ICE-like protease ICH-1. This EST clone was used to isolate a full length cDNA that encoded a protein of 199 amino acids with a predicted molecular mass of 22 kDa (SEQ ID NO:2). Given its sequence and interactions (see below), this molecule was designated RAIDD (for RIP-Associated ICH-1/CED-3 homologous protein with a Death Domain) (SEQ ID NO:2). A BLAST search revealed that this was a novel molecule possessing two domains that had distinct homologies. Residues 8–80 displayed statistically significant homology (p<0.001) with the prodomains of the human ICE-like protease ICH-1 (SEQ ID NO:3) and the *C. elegans* death protease CED-3 (SEQ ID NO:4) (FIG. 2B). Residues 123–194 encoded a C terminal Death Domain (DD) with significant homology to other DD-containing adaptor molecules (SEQ ID NOs:5, 6 and 7) (FIG. 2C). Northern blot analysis revealed RAIDD to be constitutively expressed as a 1.35 kb transcript in all adult and fetal tissues examined with substantial expression in adult heart, testis, liver, skeletal muscle, fetal liver and kidney.

The homology between the N terminal domain (NTD) of RAIDD and the prodomains of ICH-1 and CED-3 suggested that RAIDD likely binds ICH-1 and CED-3 through a homophilic mechanism using this homologous interaction domain. This notion was investigated by examining the interaction of $^{35}$S-labeled mammalian ICE/ced-3 family members with immobilized RAIDD in vitro. In keeping with the hypothesis, RAIDD specifically associated with ICH-1 but not with the other mammalian ICE-like proteases tested (i.e., ICE, TX, ICE-LAP6, ICE-LAP3, Yama and Mch2α). To confirm whether this binding was mediated by a NTD-prodomain interaction, deletion mutants of ICH-1 and RAIDD were utilized. ICH-1 bound a truncated form of RAIDD encoding only the NTD (amino acid residues 1–117 in SEQ ID NO:2), but failed to associate with a version encoding just the DD (amino acid residues 95–199 in SEQ ID NO:2). Conversely, ICH-1 without the prodomain (amino acid residues 141–436 of ICH-1) failed to associate with RAIDD while the prodomain alone (amino acid residues 1–140 of ICH-1) bound well. These results were subsequently confirmed by in vitro testing where transfected 293 cell lysates were immunoprecipitated for RAIDD (Flag epitope-tagged) and associating molecules detected by immunoblotting. To ask if an analogous interaction occurred with CED-3, 293 cells were cotransfected with expression constructs encoding CED-3 and RAIDD or a truncated form of RAIDD lacking the NTD. RAIDD, but not its deleted counterpart, associated with CED-3. Taken together, these results argue for a model in which the NTD by a homophilic mechanism selectively associates with ICE/ced-3 family members by binding to the prodomain.

Figure 4:
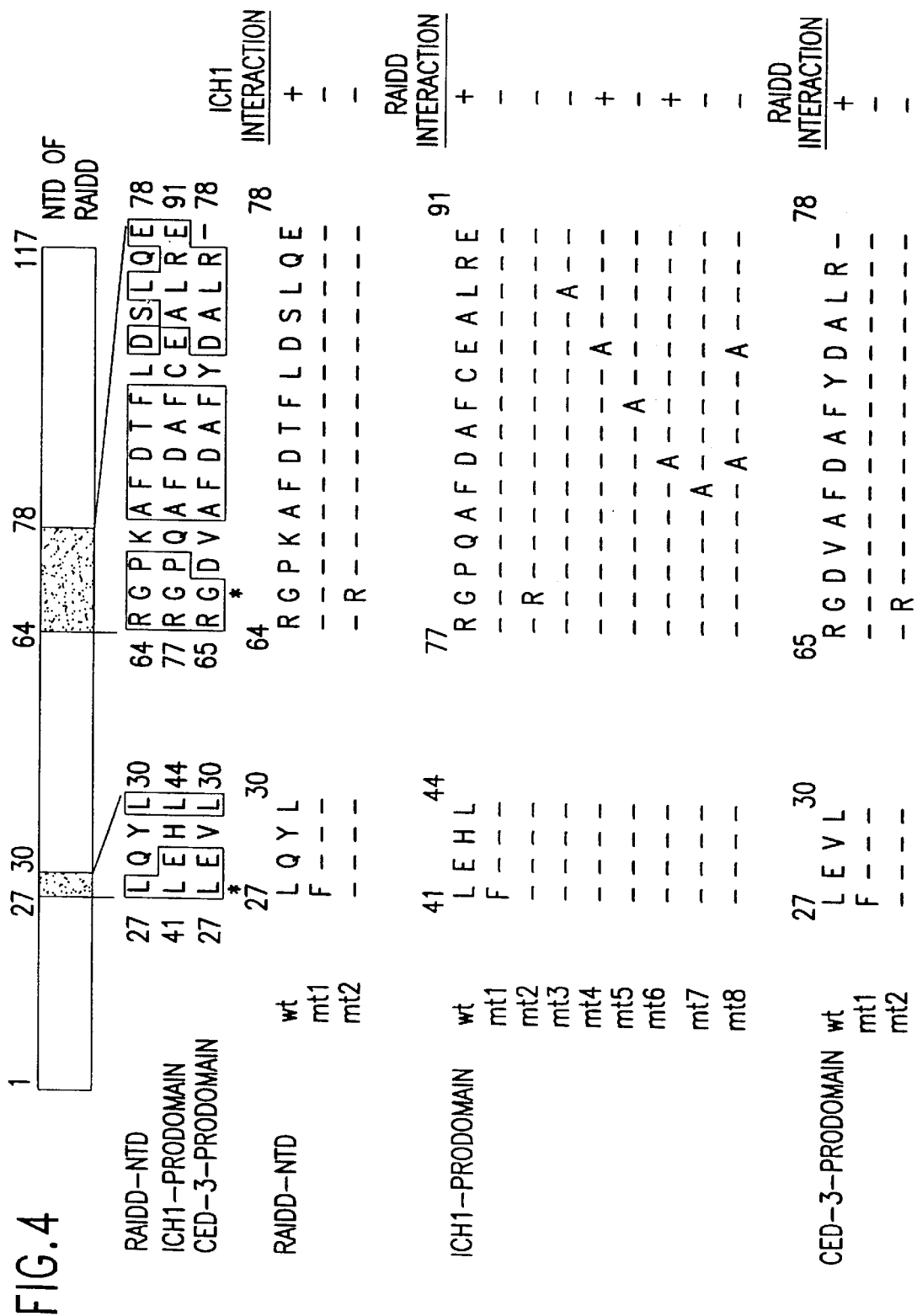
FIG. 4 shows the result of mutational analysis of the N-terminal domain (NTD) in RAIDD and ICH-1. In vitro translated $^{35}$S-labeled test proteins were incubated with either His-tagged RAIDD immobilized onto $Ni^{2+}$ beads or ICH-1 proteins bound to protein G-Sepharose. Alignment shows the regions of sequence similarity that surround the two known inactivating mutations in the prodomain of ced-3 (n1040 and n718, asterisked). Amino acids contained within each segment are numbered. Point mutations are shown as altered amino acid residues aligned to the corresponding wild type amino acid. + indicates significant binding while – indicates binding that was no different from background.

To further characterize the NTD-prodomain interaction, binding studies were performed to test the association of wild type molecules with corresponding $^{35}$S-labeled point mutants within the prodomain of ICH-1 and CED-3 or the NTD of RAIDD (FIG. 4). Mutations were introduced in residues highly conserved in all three molecules. More important, however, were alterations in residues $Leu_{27}$ and $Gly_{65}$ in the prodomain of CED-3 as these correspond to inactivating mutations of the ced-3 gene in *C. elegans* (n1040 and n718) (Ellis, H. M. & Horvitz, H. R., Cell 44:817–829 (1986); Shaham, S. & Horvitz, H. R., *Genes and Development* 10:578–591 (1996)). Additionally, residues corresponding to $Leu_{27}$ and $Gly_{65}$ in CED-3 were also mutated in RAIDD and ICH-1 (FIG. 4). In all instances where $Leu_{27}$ and $Gly_{65}$ were mutated, binding was abolished, highlighting the importance of these residues in mediating the prodomain-NTD interaction (FIG. 4). It is therefore tempting to speculate that just such a disruption might be the biochemical basis for the CED-3 inactivating mutations (n1040 and n718). Mutation of conserved hydrophobic residues in the ICH-1 prodomain including $F_{82}$, $F_{85}$ and $L_{89}$ (mt7, mt5 and mt3) abolished binding to the NTD of RAIDD. Surprisingly, it took the mutation of both conserved negatively charged residues ($D_{83}$ and $E_{87}$, mt8) to eliminate binding (FIG. 4).

Having established interactions undertaken by the NTD of RAIDD, we asked which DD-containing molecules were engaged by the DD of RAIDD. Initially, we examined all five known mammalian DD-containing proteins implicated in apoptosis (Cleveland, J. L. & Thle, J. N., *Cell* 81:479–482 (1995)). As RAIDD did not directly bind in vitro to either of the two DD-containing receptors (Fas or TNFR-1) (data not shown), we asked if it might bind to the DD-containing receptor associated molecules (FADD, TRADD, or RIP). RAIDD specifically bound RIP but not FADD or TRADD in vivo. However, in the concomitant presence of RIP, RAIDD was able to complex with TRADD. Since RIP is a component of the TNFR-1 signaling complex (Hsu, H. et al., *Immunity* 4:387–396 (1996)), it was conceivable that it could recruit RAIDD to the signaling complex. RAIDD, in turn, would be positioned to recruit ICH-1 and thereby establish a direct physical link to the effector ICE/CED-3-like death proteases. To test whether such a relay of signaling proteins could indeed be assembled, 293 cells were transiently transfected with expression vectors encoding TNFR-1, DD-containing adaptor molecules (TRADD, RIP, RAIDD, FADD), ICH-1, and ICE as a control. As anticipated, TNFR-1 complexed with RAIDD in the presence of TRADD and RIP, and through RAIDD, ICH-1 was recruited to the signaling complex. Next, we asked whether RAIDD, besides engaging the death pathway, could also induce NF-kB activation since its upstream partner, RIP, is capable of engaging both pathways (Hsu, H. et al., *Immunity* 4:387–396 (1996)). Transfected RAIDD did not activate an NF-kB reporter construct (data not shown), consistent with a primary role in apoptosis. These results suggest that RAIDD can potentially function as an adaptor molecule recruiting the death protease ICH-1 to the TNFR-1 signaling complex.

Figure 5:
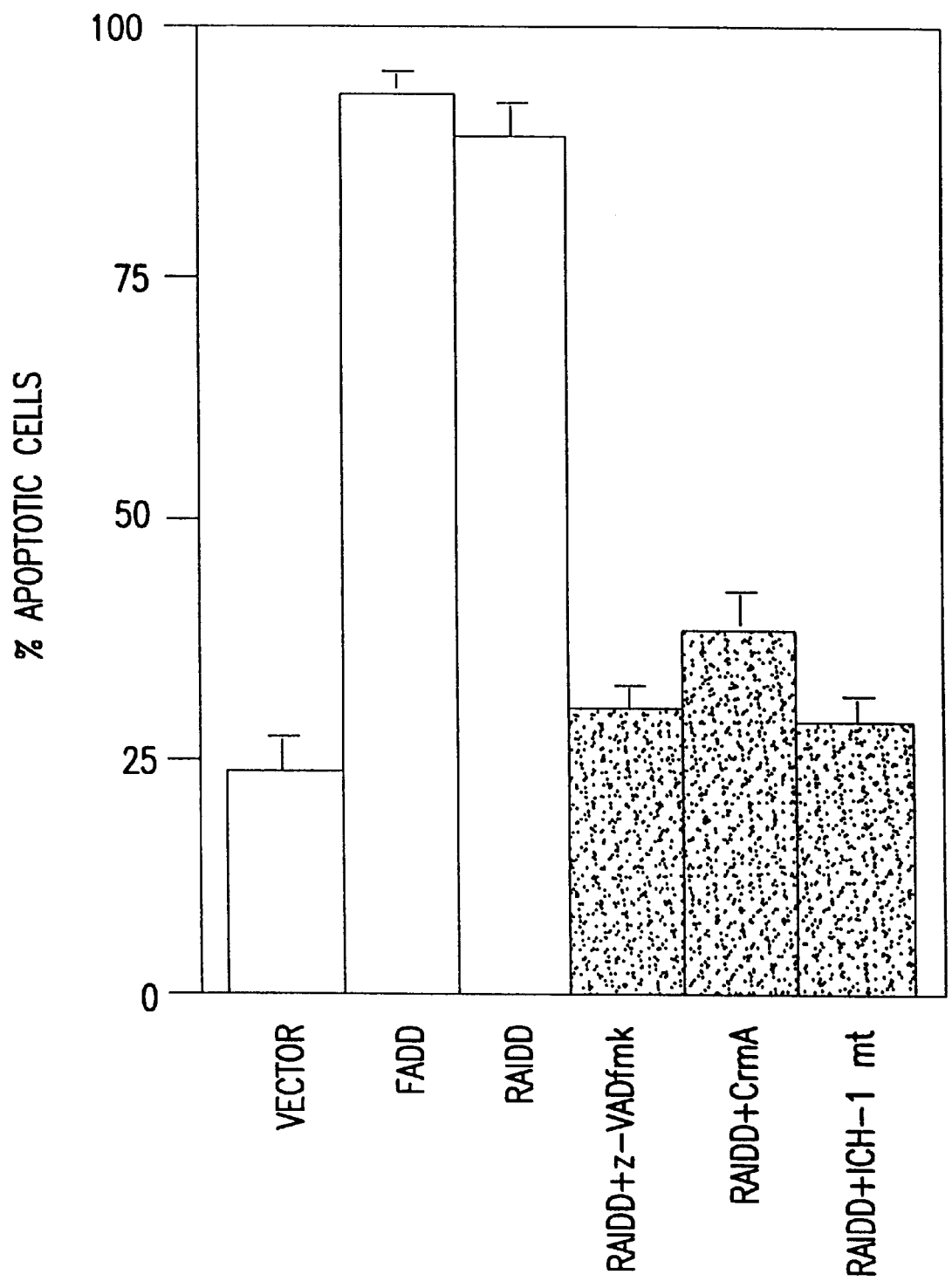
FIG. 5 shows that overexpression of RAIDD induces apoptosis which is inhibitable by CrmA, the broad spectrum ICE family inhibitor z-VAD-fmk, and a catalytically inactive version of ICH-1 ($Cys_{302}$ to Ala). The data (mean plus or minus standard error of the mean) shown are the percentage of apoptotic cells as a function of the total number of cells counted.

To address the functional role of RAIDD in apoptosis, MCF-7 cell lines were transiently transfected with a RAIDD expression construct Transfected cells underwent an apoptotic demise which was inhibitable by the broad spectrum ICE peptide inhibitor z-VAD-ink, a poxvirus encoded serpin known to inhibit apoptosis, CrmA and catalytically inactive ICH-1 that presumably behaved as a dominant negative by competing out endogenous ICH-1 (FIG. 5). The ability of dominant negative ICH-1 to block RAIDD-induced cell death gave functional credence to the biochemical interaction. However, neither mutant ICH-1 or various putative dominant negative versions of RAIDD were able to block TNFR-1 induced cell death (data not shown) presumably due to the unimpeded functioning of the alternate TRADD-FADD-FLICE death pathway.

It is unclear why two seemingly redundant pathways would be deployed by a single receptor, but differential cell or tissue specific utilization remain a distinct possibility. More importantly, however these studies illuminate how prodomain interactions can impart binding specificity, a prerequisite for the assembly of a functioning death machine.

Methods cDNA Cloning. Sequence corresponding in the pro-domain of ICH-1 was used to screen the NCBI GenBank™ EST database using established expressed-sequence-tag methods. Several overlapping clones were identified as having statistically significant homology (p<0.001) to the pro-domain of ICH-1. One such clone, I.M.A.G.E. Consortium CloneID 109053 (Lennon, G. et al., *Genomics* 33:151–152 (1996)) was characterized further and subjected to both automated and manual DNA sequencing. Additionally, a human K562 cell line cDNA library (Dr. John Lowe, University of Michigan) was screened with a $^{32}$P-labeled Pac 1/EcoR1 restriction fragment of the EST clone (Sambrook et al., supra). Hybridizing clones were characterized by automated DNA sequencing. Sequence assembly, comparison and alignment were performed using DNASTAR software.

Northern Blot analysis. Adult and fetal human multiple tissue Northern blots (Clonetech, Palo Alto, Calif.) were hybridized according to the manufacturer's instructions with the same $^{32}$P-labeled probe used for library screening.

Expression Vectors. Mammalian cell expression vectors encoding AU1-FADD, FLAG-TNFR1, Myc-TRADD and Myc-RIP have been described previously (Hsu, H. et al., *Immunity* 4:387–396 (1996); Chinnaiyan, A. M. et al., *Cell* 81:505–12 (1995)). AU1-RAIDD or FLAG-RAIDD was generated by PCR using custom oligonucleotide primers encoding the AU1 or FLAG epitope. Amplified fragments were cloned into the mammalian expression vector pcDNA3 (Invitrogen). In-frame deletion mutants were generated by PCR with or without an N-terminal AU1 epitope and subsequently subcloned into pcDNA3. Point mutations were created by site-directed mutagenesis using a two-step PCR method (Higuchi, R. et al., *Nucleic Acids Research* 16:7251–7367 (1988)) and confirmed by sequence analysis. Catalytically inactive ICH-1 was created by mutating the active site cysteine$_{302}$ to alanine.

In Vitro Binding Assay. Constructs encoding His-tagged proteins (FADD-DN, RAIDD, RAIDD-N (amino acid residues 1–117), RAIDD-DD (amino acid residues 95–199)) were prepared in the prokaryotic expression vector pET23b (Novagen). The tagged proteins were expressed, purified, and immobilized into Ni$^{2+}$ beads according to standard methodology. The GST-Fas and TNFR-1 fusion proteins were prepared as described previously (Chinnaiyan, A. M. et al., *Cell* 81:505–12 (1995)). $^{35}$S-labeled proteins were obtained by in vitro transcription/translation using the TNT T7-coupled reticulocyte lysate system (Promega).

Following translation, equivalent amounts of $^{35}$S-labeled proteins (ICE, TX, ICE-LAP6, ICE-LAP3, ICH-1, Δpro-ICH-1 (amino acid residues 141–436), pro-ICH-1 (amino acid residues 1–140), Yama and Mch2α) were incubated with His-tagged proteins or GST-fusion proteins immobilized into Ni$^{2+}$ beads or glutathione beads, respectively, as described in prior publications (Chinnaiyan, A. M. et al., *Cell* 81:505–12 (1995); Muzio, M. et al., *Cell* 85:817–827 (1996)). Beads were washed, boiled in SDS sample buffer, eluted proteins resolved by SDS-PAGE and visualized following autoradiography.

Alternatively, ICH-1 protein was produced in human 293 embryonic kidney cells transfected with the AU1-ICH-1 expression construct In Vivo Binding Assay. 293 cells were transfected with combinations of expression constructs encoding FLAG-RAIDD and one of the following proteins: AU1-ICH-1, AU1-pro-ICH-1 (amino acids 141–436) or AU1-ICE as a control. FLAG-CED-3 was cotransfected with either the death domain of RAIDD (AU1-tagged, amino acids 123–199) or the full length molecule (AU1-RAIDD). Cleared cell lysates were immunoprecipitated using anti-FLAG antibody and analyzed by immunoblotting with either anti-AU1 MAb or anti-RAIDD antipeptide antibody (produced in response to a synthetic peptide comprising amino acid residues 99 to 117 in SEQ ID NO:2).

Transfection, Coimmunoprecipitation and Western Analysis. 2993 cells were transiently transfected with indicated plasmids, lysed in 1 ml lysis buffer (50 mM Tris [pH 7.6], 150 mM NaCl, 0.1% NP-40) and incubated either with mouse control IgG or anti-FLAG MAb. Immune complexes were precipitated by the addition of protein G-Sepharose (Sigma). Following extensive washing, the Sepharose beads were boiled in sample buffer eluted proteins were processed as described previously (O'Rourke, K. M. et al., *J. of Biol. Chem.* 267:24921–24924 (1992)).

On Overexpressed RAIDD and ICH-1 are Recruited to the TNFR1 Signaling Complex. 293 cells were transfected with expression vectors expressing either Flag-TNFR1 or Flag-RAIDD and one or more of the following proteins: myc-RIP, myc-TRADD, AU1-FADD, AU1-ICE and AU1-ICH1. Detergent extracts were immunoprecipitated with either control mouse IgG or anti-FLAG MAb. Co-precipitating proteins were analyzed by immunoblotting with anti-epitope tag antibody (anti-myc and anti-AU1 anti-AU1 or RAIDD antipeptide antibody).

Apoptosis Assay. MCF-7 human breast carcinoma cells, CriA expressing stable cell lines (Tewari, M. & Dixit, V. M., *J. Biol. Chem.* 270:3255–60 (1995)), or 293-EBNA cells were transiently transfected with 0.25 µg of the reporter plasmid pCMV β-galactosidase plus 1.5 µg of test plasmid encoding either FADD or RAIDD. The broad spectrum ICE family inhibitor z-VAD-fmk (Enzyme Systems Products) was added to the cells at a concentration of 20 µm, 5 hours following transfection. Forty eight hours later, the assay was performed as described previously (Chinnaiyan, A. M. et al., *Cell* 81:505–12 (1995)).

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated polynucleotide comprising a nucleotide sequence encoding an amino acid sequence at least 95% identical to amino acids 2 to 199 of SEQ ID NO:2,
    wherein % identity is determined using the Bestfit program with parameters that calculate % identity over the full length of amino acids 2 to 199 of SEQ ID NO:2 and that allow gaps of up to 5% of the total number of residues in amino acids 2 to 199 of SEQ ID NO:2;
    wherein said polynucleotide encodes a polypeptide which either induces apoptosis or generates antibody that binds the full length RAIDD protein.

2. The isolated polynucleotide of claim 1, comprising a nucleotide sequence encoding amino acids 2 to 199 of SEQ ID NO:2.

3. The isolated polynucleotide of claim 2, comprising nucleotides 70 to 63 of SEQ ID NO:1.

4. The isolated polynucleotide of claim 1, wherein said amino acid sequence is at least 95% identical to amino acids 1 to 199 of SEQ ID NO:2;
    wherein % identity is determined using the Bestfit program with parameters that calculate % identity over the full length of amino acids 1 to 199 of SEQ ID NO:2 and that allow gaps of up to 5% of the total number of residues in amino acids 1 to 199 of SEQ ID NO:2.

5. The isolated polynucleotide of claim 4, comprising a nucleotide sequence encoding amino acids 1 to 199 of SEQ ID NO:2.

6. The isolated polynucleotide of claim 5, comprising nucleotides 67 to 663 of SEQ ID NO:1.

7. The isolated polynucleotide of claim 1, further comprising a heterologous polynucleotide.

8. The isolated polynucleotide of claim 7, wherein said heterologous polynucleotide encodes a heterologous polypeptide.

9. A method of producing a vector that comprises inserting the isolated polynucleotide of claim 1 into a vector.

10. A vector comprising the isolated polynucleotide of claim 1.

11. The vector of claim 10, wherein said polynucleotide is operably associated with a heterologous regulatory sequence.

12. A host cell comprising the isolated polynucleotide of claim 1.

13. The host cell of claim 12, wherein said isolated polynucleotide is operably associated with a heterologous regulatory sequence.

14. A method of producing a polypeptide that comprises culturing the host cell of claim 13 under conditions such that said polypeptide is expressed, and recovering said polypeptide.

15. An isolated polynucleotide comprising a nucleotide sequence encoding an amino acid sequence at least 95% identical to the mature amino acid sequence encoded by the cDNA clone in ATCC Deposit No. 97824,
    wherein % identity is determined using the Bestfit program with parameters that calculate % identity over the full length of the mature amino acid sequence encoded by the cDNA clone in ATCC Deposit No. 97824 and that allow gaps of up to 5% of the total number of residues of the mature amino acid sequence encoded by the cDNA clone in ATCC Deposit No. 97824;
    wherein said polynucleotide encodes a polypeptide which either induces apoptosis or generates antibody that binds the full length RAIDD protein.

16. The isolated polynucleotide of claim 15, comprising a nucleotide sequence encoding the mature amino acid sequence encoded by the cDNA clone in ATCC Deposit No. 97824.

17. The isolated polynucleotide of claim 15, wherein said amino acid sequence is at least 95% identical to the complete amino acid sequence encoded by the cDNA clone in ATCC Deposit No. 97824;
    wherein % identity is determined using the Bestfit program with parameters that calculate % identity over the full length of the complete amino acid sequence encoded by the cDNA clone in ATCC Deposit No. 97824 and that allow gaps of up to 5% of the total number of residues of the complete amino acid sequence encoded by the cDNA clone in ATCC Deposit No. 97824.

18. The isolated polynucleotide of claim 17, comprising the complete amino acid sequence encoded by the cDNA clone in ATCC Deposit No. 97824.

19. The isolated polynucleotide of claim 15, further comprising a heterologous polynucleotide.

20. The isolated polynucleotide of claim 19, wherein said heterologous polynucleotide encodes a heterologous polypeptide.

21. A method of producing a vector that comprises inserting the isolated polynucleotide of claim 15 into a vector.

22. A vector comprising the isolated polynucleotide of claim 15.

23. The vector of claim 22, wherein said polynucleotide is operably associated with a heterologous regulatory sequence.

24. A host cell comprising the isolated polynucleotide of claim 15.

25. The host cell of claim 24, wherein said isolated polynucleotide is operably associated with a heterologous regulatory sequence.

26. A method of producing a polypeptide that comprises culturing the host cell of claim 25 under conditions such that said polypeptide is expressed, and recovering said polypeptide.

27. An isolated polynucleotide comprising 300 contiguous nucleotides of the coding region of SEQ ID NO:1 or the complementary sequence thereof.

28. The isolated polynucleotide of claim 27, comprising 350 contiguous nucleotides of the coding region of SEQ ID NO:1 or the complementary sequence thereof.

29. The isolated polynucleotide of claim 28, comprising 400 contiguous nucleotides of the coding region of SEQ ID NO:1 or the complementary sequence thereof.

30. The isolated polynucleotide of claim 29, comprising 450 contiguous nucleotides of the coding region of SEQ ID NO:1 or the complementary sequence thereof.

31. The isolated polynucleotide of claim 27, further comprising a heterologous polynucleotide.

32. The isolated polynucleotide of claim 31, wherein said heterologous polynucleotide encodes a heterologous polypeptide.

33. A method of producing a vector that comprises inserting the isolated polynucleotide of claim 27 into a vector.

34. A vector comprising the isolated polynucleotide of claim 27.

35. The vector of claim 34, wherein said polynucleotide is operably associated with a heterologous regulatory sequence.

36. A host cell comprising the isolated polynucleotide of claim 27.

37. The host cell of claim 36, wherein said isolated polynucleotide is operably associated with a heterologous regulatory sequence.

38. A method of producing a polypeptide that comprises culturing the host cell of claim 37 under conditions such that said polypeptide is expressed, and recovering said polypeptide.

39. An isolated polynucleotide comprising 500 contiguous nucleotides of the coding region of SEQ ID NO:1 or the complementary sequence thereof.

40. The isolated polynucleotide of claim 39, further comprising a heterologous polynucleotide.

41. The isolated polynucleotide of claim 40, wherein said heterologous polynucleotide encodes a heterologous polypeptide.

42. A method of producing a vector that comprises inserting the isolated polynucleotide of claim 39 into a vector.

43. A vector comprising the isolated polynucleotide of claim 39.

44. The vector of claim 43, wherein said polynucleotide is operably associated with a heterologous regulatory sequence.

45. A host cell comprising the isolated polynucleotide of claim 39.

46. The host cell of claim 45, wherein said isolated polynucleotide is operably associated with a heterologous regulatory sequence.

47. A method of producing a polypeptide that comprises culturing the host cell of claim 46 under conditions such that said polypeptide is expressed, and recovering said polypeptide.

48. An isolated polynucleotide comprising a nucleotide sequence encoding amino acids 168 to 178 of SEQ ID NO:2.

49. The isolated polynucleotide of claim 48, comprising a nucleotide sequence encoding amino acids 123 to 194 of SEQ ID NO:2.

50. The isolated polynucleotide of claim 49, consisting of a nucleotide sequence encoding amino acids 118 to 199 of SEQ ID NO:2.

51. The isolated polynucleotide of claim 50, consisting of a nucleotide sequence encoding amino acids 99 to 199 of SEQ ID NO:2.

52. The isolated polynucleotide of claim 49, comprising a nucleotide sequence encoding amino acids 95 to 199 of SEQ ID NO:2.

53. The isolated polynucleotide of claim 48, further comprising a heterologous polynucleotide.

54. The isolated polynucleotide of claim 53 wherein said heterologous polynucleotide encodes a heterologous polypeptide.

55. A method of producing a vector that comprises inserting the isolated polynucleotide of claim 48 into a vector.

56. A vector comprising the isolated polynucleotide of claim 48.

57. The vector of claim 56, wherein said polynucleotide is operably associated with a heterologous regulatory sequence.

58. A host cell comprising the isolated polynucleotide of claim 48.

59. The host cell of claim 58, wherein said isolated polynucleotide is operably associated with a heterologous regulatory sequence.

60. A method of producing a polypeptide that comprises culturing the host cell of claim 59 under conditions such that said polypeptide is expressed, and recovering said polypeptide.

61. An isolated polynucleotide comprising a nucleotide sequence encoding amino acids 8 to 80 of SEQ ID NO:2.

62. The isolated polynucleotide of claim 61, further comprising a heterologous polynucleotide.

63. The isolated polynucleotide of claim 62, wherein said heterologous polynucleotide encodes a heterologous polypeptide.

64. A method of producing a vector that comprises inserting the isolated polynucleotide of claim 61 into a vector.

65. A vector comprising the isolated polynucleotide of claim 61.

66. The vector of claim 65, wherein said polynucleotide is operably associated with a heterologous regulatory sequence.

67. A host cell comprising the isolated polynucleotide of claim 61.

68. The host cell of claim 67, wherein said isolated polynucleotide is operably associated with a heterologous regulatory sequence.

69. A method of producing a polypeptide that comprises culturing the host cell of claim 68 under conditions such that said polypeptide is expressed, and recovering said polypeptide.

70. An isolated polynucleotide comprising a nucleotide sequence encoding an amino acid sequence at least 95% identical to a reference amino acid sequence selected from the group consisting of:

(a) amino acids 8 to 80 of SEQ ID NO:2;

(b) amino acids 123 to 194 of SEQ ID NO:2;

(c) amino acids 1 to 117 of SEQ ID NO:2; and (d) amino acids 95 to 199 of SEQ ID NO:2;

wherein % identity is determined using the Bestfit program with parameters that calculate % identity over the full length of the reference amino acid sequence and that allow gaps of up to 5% of the total number of residues of the reference amino acid sequence;

wherein said polynucleotide encodes a polypeptide which either induces apoptosis or generates antibody that binds the full length RAIDD protein.

71. The isolated polynucleotide of claim 70, wherein said reference amino acid sequence is (a).

72. The isolated polynucleotide of claim 70, wherein said reference amino acid sequence is (b).

73. The isolated polynucleotide of claim 70, wherein said reference amino acid sequence is (c).

74. The isolated polynucleotide of claim 70, wherein said reference amino acid sequence is (d).

75. The isolated polynucleotide of claim 70, further comprising a heterologous polynucleotide.

76. The isolated polynucleotide of claim 75, wherein said heterologous polynucleotide encodes a heterologous polypeptide.

77. A method of producing a vector that comprises inserting the isolated polynucleotide of claim 70 into a vector.

78. A vector comprising the isolated polynucleotide of claim 70.

79. The vector of claim 78, wherein said polynucleotide is operably associated with a heterologous regulatory sequence.

80. A host cell comprising the isolated polynucleotide of claim 70.

81. The host cell of claim 80, wherein said isolated polynucleotide is operably associated with a heterologous regulatory sequence.

82. A method of producing a polypeptide that comprises culturing the host cell of claim 81 under conditions such that said polypeptide is expressed, and recovering said polypeptide.

83. An isolated polynucleotide comprising a nucleotide sequence encoding at least 30 contiguous amino acids of amino acids 95 to 199 of SEQ ID NO:2;

wherein said polynucleotide encodes a polypeptide which generates antibody that binds the full length RAIDD protein.

84. The isolated polynucleotide of claim 83, further comprising a heterologous polynucleotide.

85. The isolated polynucleotide of claim 84, wherein said heterologous polynucleotide encodes a heterologous polypeptide.

86. A method of producing a vector that comprises inserting the isolated polynucleotide of claim 83 into a vector.

87. A vector comprising the isolated polynucleotide of claim 83.

88. The vector of claim 87, wherein said polynucleotide is operably associated with a heterologous regulatory sequence.

89. A host cell comprising the isolated polynucleotide of claim 83.

90. The host cell of claim 89, wherein said isolated polynucleotide is operably associated with a heterologous regulatory sequence.

91. A method of producing a polypeptide that comprises culturing the host cell of claim 90 under conditions such that said polypeptide is expressed, and recovering said polypeptide.

92. The isolated polynucleotide of claim 83 which comprises a nucleotide sequence encoding at least 50 contiguous amino acids of amino acids 95 to 199 of SEQ ID NO:2.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 1160 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS (B) LOCATION: 67..663

(xi) SEQUENCE DESCRIPTION: SEQ ID NO:1:

```
AACAGTCAGG ATTCCGGTTG CAGTTTTTCT CCCCCGCCCC AAAGATACGT GGTTGCAGAC      60

GGAGAA ATG GAG GCC AGA GAC AAA CAA GTA CTC CGC TCA CTT CGC CTG        108
       Met Glu Ala Arg Asp Lys Gln Val Leu Arg Ser Leu Arg Leu
        1               5                  10

GAG CTG GGT GCA GAG GTA TTG GTG GAG GGA CTG GTT CTT CAG TAC CTC       156
Glu Leu Gly Ala Glu Val Leu Val Glu Gly Leu Val Leu Gln Tyr Leu
 15              20                  25                  30

TAC CAG GAA GGA ATC TTG ACG GAA AAC CAT ATT CAA GAA ATC AAT GCT       204
Tyr Gln Glu Gly Ile Leu Thr Glu Asn His Ile Gln Glu Ile Asn Ala
                35                  40                  45

CAA ACC ACA GGC CTC CGG AAA ACA ATG CTC CTG CTG GAT ATC CTA CCT       252
Gln Thr Thr Gly Leu Arg Lys Thr Met Leu Leu Leu Asp Ile Leu Pro
            50                  55                  60

TCC AGG GGC CCT AAA GCA TTT GAT ACA TTC CTA GAT TCC CTA CAG GAG       300
Ser Arg Gly Pro Lys Ala Phe Asp Thr Phe Leu Asp Ser Leu Gln Glu
        65                  70                  75

TTT CCC TGG GTC AGG GAG AAG CTG AAG AAG GCA AGG GAA GAG GCC ATG       348
Phe Pro Trp Val Arg Glu Lys Leu Lys Lys Ala Arg Glu Glu Ala Met
    80                  85                  90

ACC GAC CTG CCT GCA GGT GAC AGA TTG ACT GGG ATC CCC TCG CAC ATC       396
Thr Asp Leu Pro Ala Gly Asp Arg Leu Thr Gly Ile Pro Ser His Ile
 95                 100                 105                 110

CTC AAC AGC TCC CCA TCA GAC CGG CAG ATT AAC CAG CTG GCC CAG AGG       444
Leu Asn Ser Ser Pro Ser Asp Arg Gln Ile Asn Gln Leu Ala Gln Arg
                115                 120                 125

CTG GGC CCT GAG TGG GAG CCC ATG GTG TTG TCT CTG GGA CTG TCC CAG       492
Leu Gly Pro Glu Trp Glu Pro Met Val Leu Ser Leu Gly Leu Ser Gln
            130                 135                 140

ACG GAT ATC TAC CGC TGT AAG GCC AAC CAC CCC CAC AAC GTG CAG TCG       540
Thr Asp Ile Tyr Arg Cys Lys Ala Asn His Pro His Asn Val Gln Ser
        145                 150                 155

CAG GTG GTG GAG GCC TTC ATC CGT TGG CGG CAG CGC TTC GGG AAG CAG       588
Gln Val Val Glu Ala Phe Ile Arg Trp Arg Gln Arg Phe Gly Lys Gln
    160                 165                 170

GCC ACC TTC CAG AGC CTG CAC AAC GGG CTG CGG GCT GTG GAG GTG GAC       636
Ala Thr Phe Gln Ser Leu His Asn Gly Leu Arg Ala Val Glu Val Asp
175                 180                 185                 190

CCC TCG CTG CTC CTG CAC ATG TTG GAG TGATGGTGCC TCCAGCAACC             683
Pro Ser Leu Leu Leu His Met Leu Glu
                195

GCTGGGAGT GTGTCCCTGA GTCATGTGGG CTGAATCCTG ACTTTCACTC AGAGCAGGTG      743

GTTTTTTGTG TAGGTTTGTT TTTTATTTTT GATGATCTTC AGATGGAAGG AGAAAACAGG     803

GTTTCCACTA GACATTACTT GAAAGGCCAG ATTACTCAGC AGATCTCCCA TGTTGGCTCA     863

ACAATTCTTT GTTTTTAATT GCTTGAAGAT TGCATTGTTG TAATTGTTCA GTTTTTAAAT     923

GTGTAATGGC ATTTTAATAG ACTAGTAAAT CACAGTGGTT CCAAATATAT ACCCATATAT     983

ATATATATCC ATATATATAT CTCATGTCAT CACATTACAG GCAGGTGTCT CATATGTAAA    1043

ACATTTACCT GAATGTTGTC TGAGGACTGA ACTGTGGACT TTACTATTCA TAATGATAAA    1103

ATAATAAAAT GCGAATTACT ATAAAAAAAA AAAAAAAAAA AAAAAAAAAA AAAAAA        1160
```

(2) INFORMATION FOR SEQ ID NO:2:

(i) SEQUENCE CHARACTERISTICS:
(A) LENGTH: 199 amino acids

```
            (B) TYPE: amino acid
            (D) TOPOLOGY: linear (ii) MOLECULE TYPE: protein (xi) SEQUENCE DESCRIPTION: SEQ ID NO:2:

Met Glu Ala Arg Asp Lys Gln Val Leu Arg Ser Leu Arg Leu Glu Leu
 1               5                  10                  15

Gly Ala Glu Val Leu Val Glu Gly Leu Val Leu Gln Tyr Leu Tyr Gln
                20                  25                  30

Glu Gly Ile Leu Thr Glu Asn His Ile Gln Glu Ile Asn Ala Gln Thr
            35                  40                  45

Thr Gly Leu Arg Lys Thr Met Leu Leu Leu Asp Ile Leu Pro Ser Arg
50                  55                  60

Gly Pro Lys Ala Phe Asp Thr Phe Leu Asp Ser Leu Gln Glu Phe Pro
65                  70                  75                  80

Trp Val Arg Glu Lys Leu Lys Lys Ala Arg Glu Ala Met Thr Asp
                85                  90                  95

Leu Pro Ala Gly Asp Arg Leu Thr Gly Ile Pro Ser His Ile Leu Asn
                100                 105                 110

Ser Ser Pro Ser Asp Arg Gln Ile Asn Gln Leu Ala Gln Arg Leu Gly
                115                 120                 125

Pro Glu Trp Glu Pro Met Val Leu Ser Leu Gly Leu Ser Gln Thr Asp
130                 135                 140

Ile Tyr Arg Cys Lys Ala Asn His Pro His Asn Val Gln Ser Gln Val
145                 150                 155                 160

Val Glu Ala Phe Ile Arg Trp Arg Gln Arg Phe Gly Lys Gln Ala Thr
                165                 170                 175

Phe Gln Ser Leu His Asn Gly Leu Arg Ala Val Glu Val Asp Pro Ser
                180                 185                 190

Leu Leu Leu His Met Leu Glu
                195

(2) INFORMATION FOR SEQ ID NO:3:

(i) SEQUENCE CHARACTERISTICS:
        (A) LENGTH: 69 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:3:

Leu Lys Lys Asn Arg Val Val Leu Ala Lys Gln Leu Leu Leu Ser Glu
 1               5                  10                  15

Leu Leu Glu His Leu Leu Glu Lys Asp Ile Ile Thr Leu Glu Met Arg
                20                  25                  30

Glu Leu Ile Gln Ala Lys Val Gly Ser Phe Ser Gln Asn Val Glu Leu
            35                  40                  45

Leu Asn Leu Leu Pro Lys Arg Gly Pro Gln Ala Phe Asp Ala Phe Cys
50                  55                  60

Glu Ala Leu Arg Glu
65

(2) INFORMATION FOR SEQ ID NO:4:

(i) SEQUENCE CHARACTERISTICS:
        (A) LENGTH: 68 amino acids
```

```
          (B) TYPE: amino acid
          (C) STRANDEDNESS: single
          (D) TOPOLOGY: Not Relevant (ii) MOLECULE TYPE: peptide (xi) SEQUENCE DESCRIPTION: SEQ ID NO:4:

Leu Glu Arg Asn Ile Met Met Phe Ser Ser His Leu Lys Val Asp Glu
1               5                  10                  15

Ile Leu Glu Val Leu Ile Ala Lys Gln Val Leu Asn Ser Asp Asn Gly
            20                  25                  30

Asp Met Ile Asn Ser Cys Gly Thr Val Arg Glu Lys Arg Arg Glu Ile
        35                  40                  45

Val Lys Ala Val Gln Arg Arg Gly Asp Val Ala Phe Asp Ala Phe Tyr
50                  55                  60

Asp Ala Leu Arg
65

(2) INFORMATION FOR SEQ ID NO:5:

(i) SEQUENCE CHARACTERISTICS:
          (A) LENGTH: 74 amino acids
          (B) TYPE: amino acid
          (C) STRANDEDNESS: single
          (D) TOPOLOGY: Not Relevant (ii) MOLECULE TYPE: peptide (xi) SEQUENCE DESCRIPTION: SEQ ID NO:5:

Ile Cys Asp Asn Val Gly Lys Asp Trp Arg Arg Leu Ala Arg Gln Leu
1               5                  10                  15

Lys Val Ser Asp Thr Lys Ile Asp Ser Ile Glu Asp Arg Tyr Pro Arg
            20                  25                  30

Asn Leu Thr Glu Arg Val Arg Glu Ser Leu Arg Ile Trp Lys Asn Thr
        35                  40                  45

Glu Lys Glu Asn Ala Thr Val Ala His Leu Val Gly Ala Leu Arg Ser
50                  55                  60

Cys Gln Met Asn Leu Val Ala Asp Leu Val
65                  70

(2) INFORMATION FOR SEQ ID NO:6:

(i) SEQUENCE CHARACTERISTICS:
          (A) LENGTH: 81 amino acids
          (B) TYPE: amino acid
          (C) STRANDEDNESS: single
          (D) TOPOLOGY: Not Relevant (ii) MOLECULE TYPE: peptide (xi) SEQUENCE DESCRIPTION: SEQ ID NO:6:

Phe Ala Arg Ser Val Gly Leu Lys Trp Arg Lys Val Gly Arg Ser Leu
1               5                  10                  15

Gln Arg Gly Cys Arg Ala Leu Arg Asp Pro Ala Leu Asp Ser Leu Ala
            20                  25                  30

Tyr Glu Tyr Glu Arg Glu Gly Leu Tyr Glu Gln Ala Phe Gln Leu Leu
        35                  40                  45

Arg Arg Phe Val Gln Ala Glu Gly Arg Arg Ala Thr Leu Gln Arg Leu
50                  55                  60

Val Glu Ala Leu Glu Glu Asn Glu Leu Thr Ser Leu Ala Glu Asp Leu
65                  70                  75                  80
```

-continued

Leu (2) INFORMATION FOR SEQ ID NO:7:

(i) SEQUENCE CHARACTERISTICS:
        (A) LENGTH: 77 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:7:

```
Ile Arg Glu Asn Leu Gly Lys His Trp Lys Asn Cys Ala Arg Lys Leu
1               5                   10                  15

Gly Phe Thr Gln Ser Gln Ile Asp Glu Ile Asp His Asp Tyr Glu Arg
            20                  25                  30

Asp Gly Leu Lys Glu Lys Val Tyr Gln Met Leu Gln Lys Trp Val Met
            35                  40                  45

Arg Glu Gly Ile Lys Gly Ala Thr Val Gly Lys Leu Ala Gln Ala Leu
        50                  55                  60

His Gln Cys Ser Arg Ile Asp Leu Leu Ser Ser Leu Ile
65                  70                  75
```